United States Patent
Hematti et al.

(10) Patent No.: US 10,166,254 B2
(45) Date of Patent: Jan. 1, 2019

(54) USE OF MESENCHYMAL STEM CELL-EDUCATED MACROPHAGES TO TREAT AND PREVENT GRAFT VERSUS HOST DISEASE AND RADIATION-INDUCED INJURY

(71) Applicant: Wisconsin Alumni Research Foundation, Madison, WI (US)

(72) Inventors: Peiman Hematti, Middleton, WI (US); Myriam N. Bouchlaka, Madison, WI (US); Christian M. Capitini, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/858,896

(22) Filed: Sep. 18, 2015

(65) Prior Publication Data
US 2016/0082042 A1    Mar. 24, 2016

Related U.S. Application Data

(60) Provisional application No. 62/052,672, filed on Sep. 19, 2014.

(51) Int. Cl.
*A61K 35/15*    (2015.01)
*A61K 45/06*    (2006.01)

(52) U.S. Cl.
CPC .............. *A61K 35/15* (2013.01); *A61K 45/06* (2013.01)

(58) Field of Classification Search
CPC ................................. A61K 35/15; A61K 45/06
See application file for complete search history.

(56) References Cited

U.S. PATENT DOCUMENTS

| 8,647,678 B2 | 2/2014 | Hematti | |
| 2011/0045071 A1* | 2/2011 | Hematti | C12N 5/0645 424/484 |
| 2012/0214729 A1* | 8/2012 | Son | A61K 38/08 514/1.4 |

OTHER PUBLICATIONS

Garau et al. Radiobiology of the acute radiation syndrome. Reports of Practical Oncology and Radiotherapy 16(2011):123-130.*
Lorimore et al. Inflammatory-type responses after exposure to ionizing radiation in vivo:a mechanism for radiation-induced bystander e€ects? Oncogene (2001) 20, 7085-7095.*
Williams et al. Treatment for Radiation-Induced Pulmonary Late Effects: Spoiled for Choice or Looking in the Wrong Direction? Curr Drug Targets. Nov. 1, 2010; 11(11): 1386-1394.*
Maderna et al. Phagocytosis of apoptotic cells and the resolution of inflammation. Biochimica et Biophysica Acta 1639 (2003) 141-151. (Year: 2003).*
Wills et al. Total body irradiation:A practical review. Applied Radiation Oncology. Jun. 2016, p. 11-17 (Year: 2016).*
Giebel et al. Extreme Heterogeneity of Myeloablative Total Body Irradiation Techniques in Clinical Practice. Cancer 2014;120: p. 2760-5. (Year: 2014).*
Eaton, Erik B., and Timothy R. Varney. "Mesenchymal stem cell therapy for acute radiation syndrome: innovative medical approaches in military medicine." Military Medical Research 2.1 (2015): 1. Published online Jan. 30, 2015.
Ferrara, James LM, et al. "Graft-versus-host disease." The Lancet 373.9674 (2009): 1550-1561. Published online Mar. 11, 2009.
François, Moïra, et al. "Human MSC suppression correlates with cytokine induction of indoleamine 2, 3-dioxygenase and bystander M2 macrophage differentiation." Molecular Therapy 20.1 (Jan. 2012): 187-195.
Hu, JiangWei, et al. "Infusion of Trx-1-overexpressing hucMSC prolongs the survival of acutely irradiated NOD/SCID mice by decreasing excessive inflammatory injury." PloS one 8.11 (Nov. 2013): e78227.
Hu, K. X., et al. "The radiation protection and therapy effects of mesenchymal stem cells in mice with acute radiation injury." The British journal of radiology 83 (Jan. 2010), 52-58.
Lange, Claudia, et al. "Radiation rescue: mesenchymal stromal cells protect from lethal irradiation." PloS one 6.1 (Jan. 2011): e14486.
Le Blanc, Katarina, and Dimitrios Mougiakakos. "Multipotent mesenchymal stromal cells and the innate immune system." Nature Reviews Immunology 12.5 (May 2012): 383-396.
Maggini, Julian, et al. "Mouse bone marrow-derived mesenchymal stromal cells turn activated macrophages into a regulatory-like profile." PloS one 5.2 (Feb. 2010): e9252.
Németh, Krisztián, et al. "Bone marrow stromal cells attenuate sepsis via prostaglandin E2—dependent reprogramming of host macrophages to increase their interleukin-10 production." Nature medicine 15.1 (Jan. 2009): 42-49.
Przepiorka, D., et al. "1994 Consensus conference on acute GVHD grading." Bone marrow transplantation 15.6 (Jun. 1995): 825-828.
Shim, Sehwan, et al. "Mitigating effects of hUCB-MSCs on the hematopoietic syndrome resulting from total body irradiation." Experimental hematology 41.4 (Apr. 2013): 346-353.
Singh, Vijay K., et al. "Myeloid progenitors: A radiation countermeasure that is effective when initiated days after irradiation." Radiation research 177.6 (published online Jan. 11, 2012): 781-791.
Trivedi, Parul, and Peiman Hematti. "Derivation and immunological characterization of mesenchymal stromal cells from human embryonic stem cells." Experimental hematology 36.3 (2008): 350-359. Published online Jan. 7, 2008.
Zhang, Qun-Zhou, et al. "Human gingiva-derived mesenchymal stem cells elicit polarization of M2 macrophages and enhance cutaneous wound healing." Stem Cells 28.10 (Oct. 2010): 1856-1868.

* cited by examiner

*Primary Examiner* — Taeyoon Kim
(74) *Attorney, Agent, or Firm* — Quarles & Brady LLP

(57) ABSTRACT

The present invention relates to methods for treating and preventing graft-versus-host disease (GVHD) and radiation-induced tissue damage or organ failure. More particularly, methods of the present invention comprise administering a therapeutically effective amount of mesenchymal stem cell-educated macrophages (MEMs) to a subject to treat or prevent GVHD, bone marrow failure, radiation-induced tissue damage or organ failure, or a condition associated with aberrant inflammation.

8 Claims, 13 Drawing Sheets
(12 of 13 Drawing Sheet(s) Filed in Color)

FIGS. 1A-B
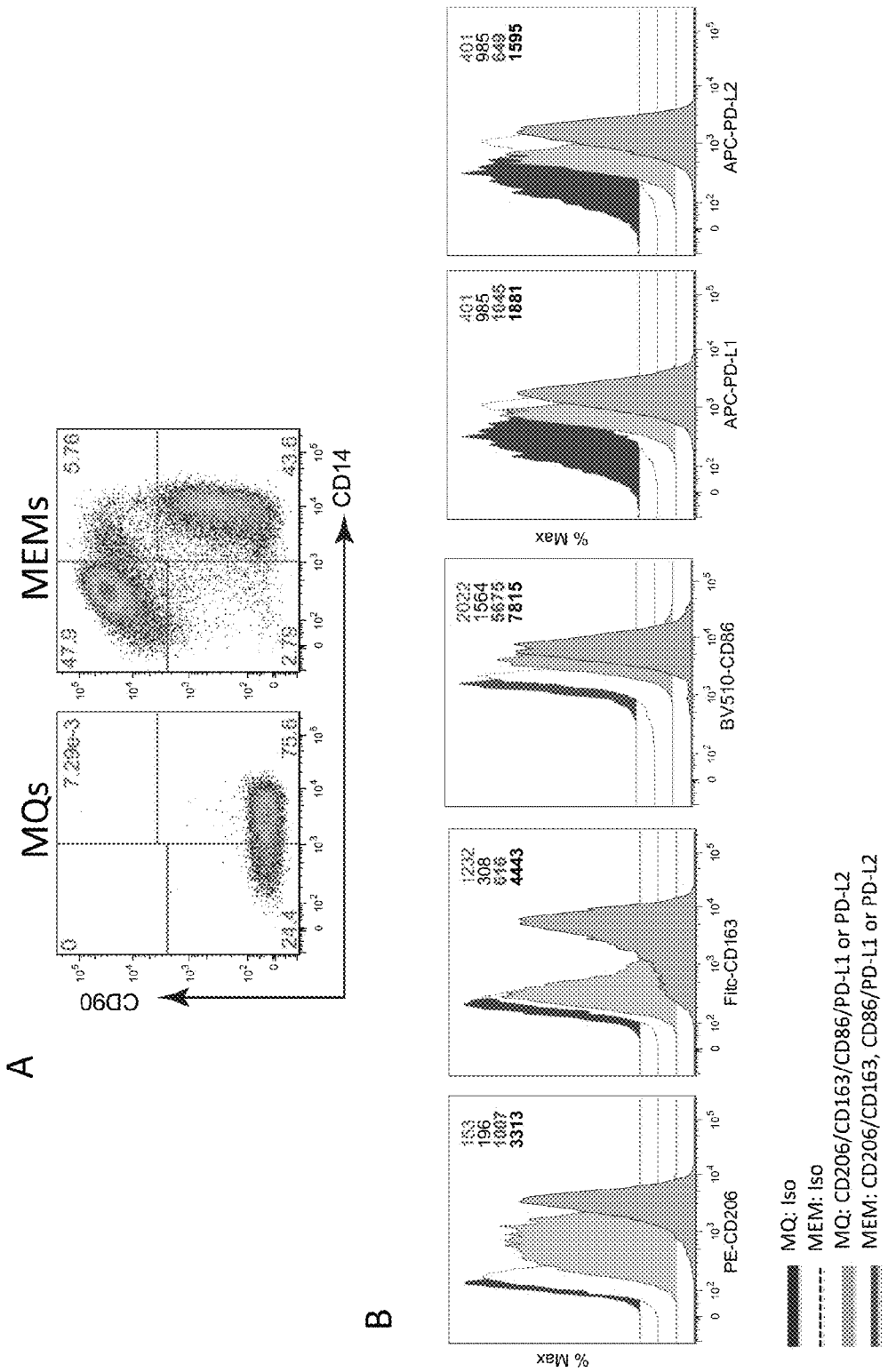

FIGS. 3A-D
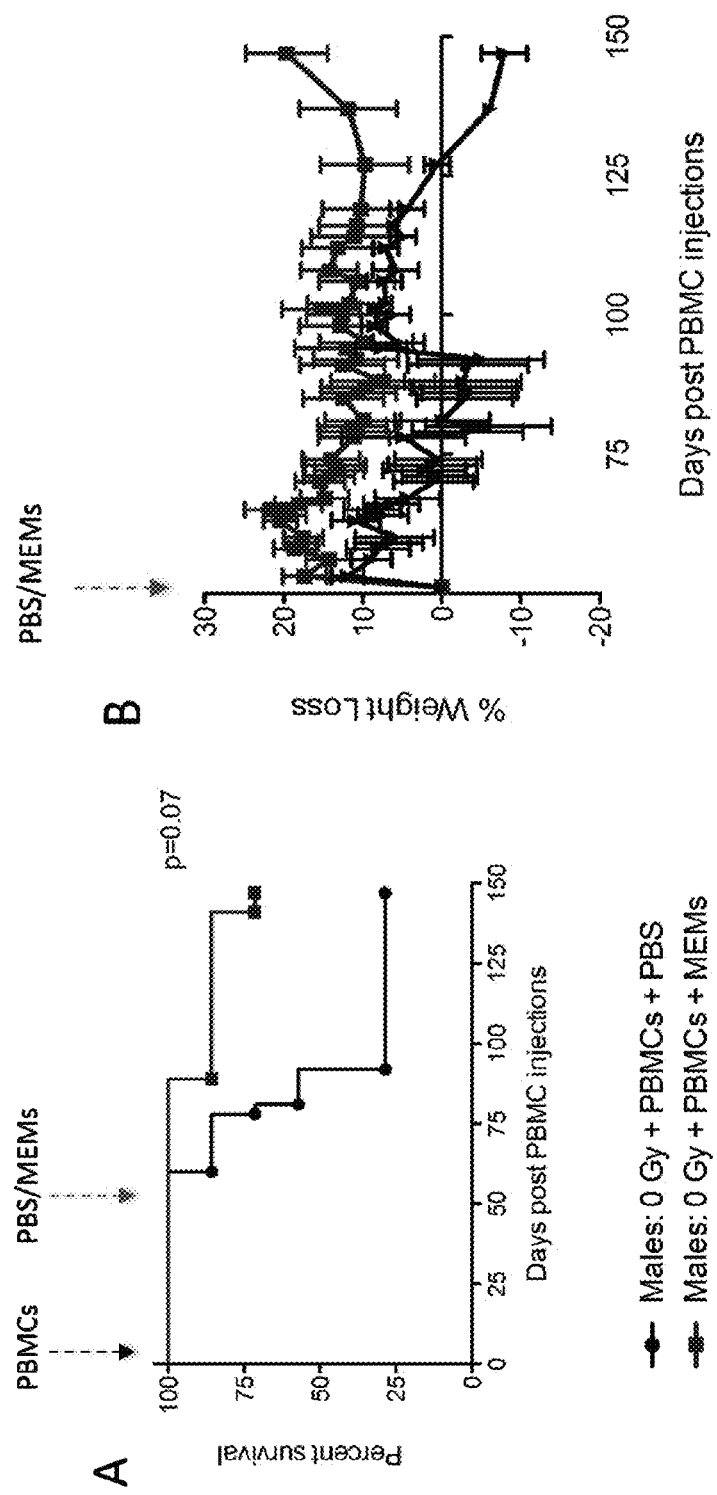

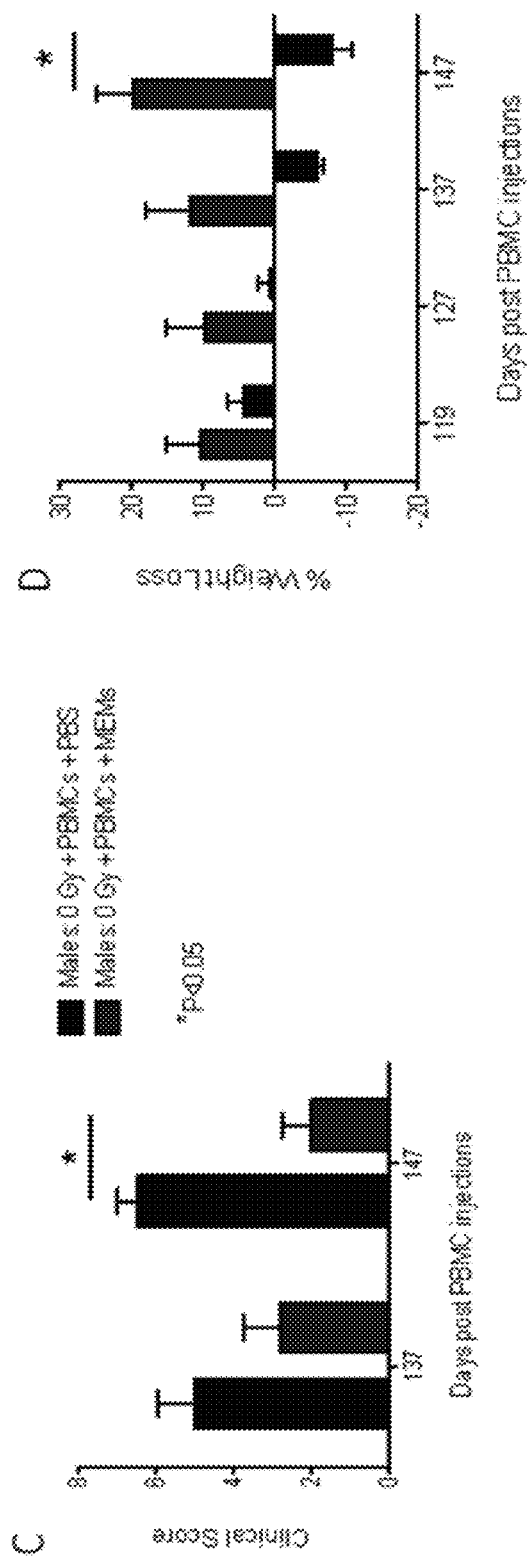
FIGS. 3A-D, CONTINUED

FIGS. 4A-C
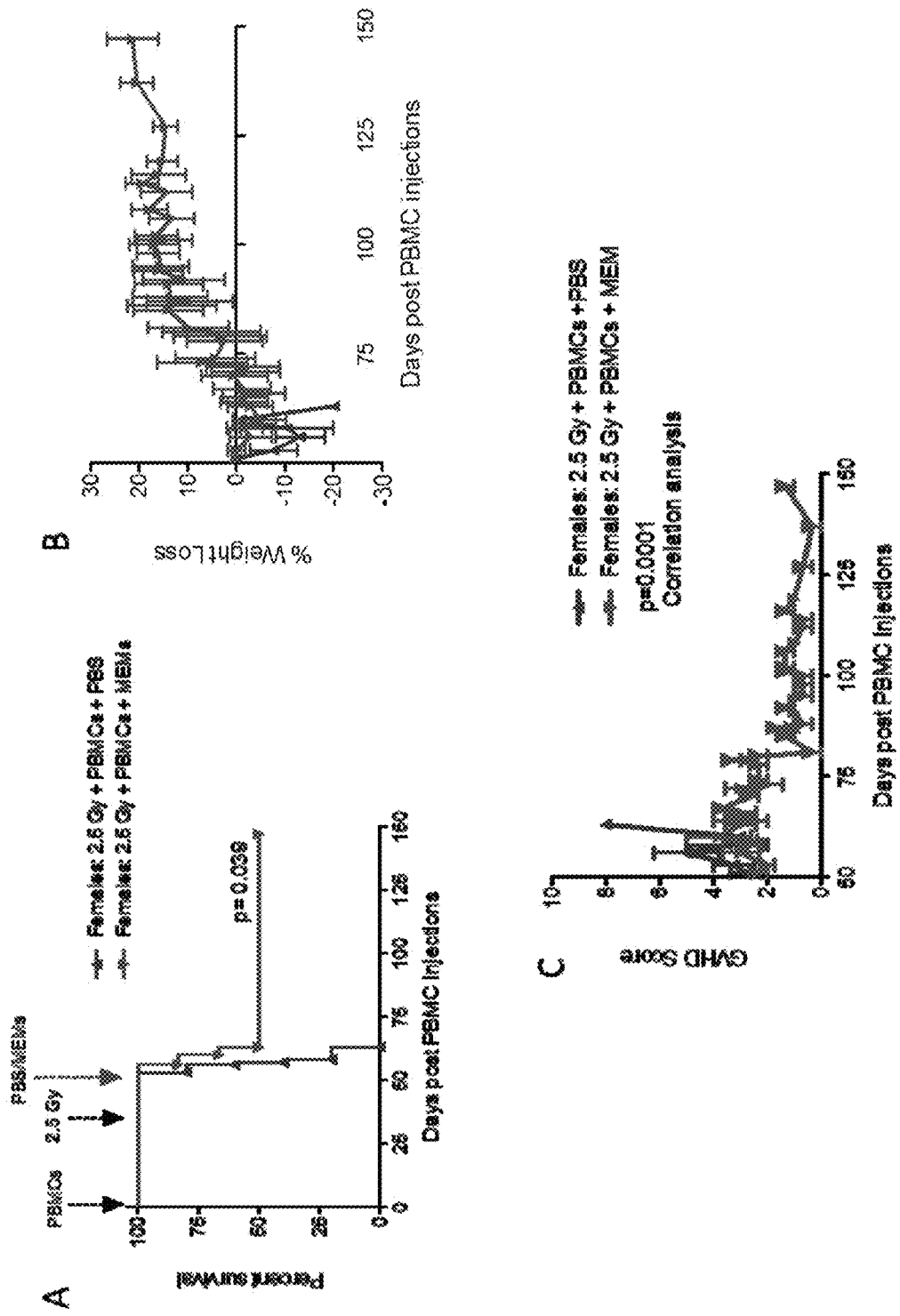

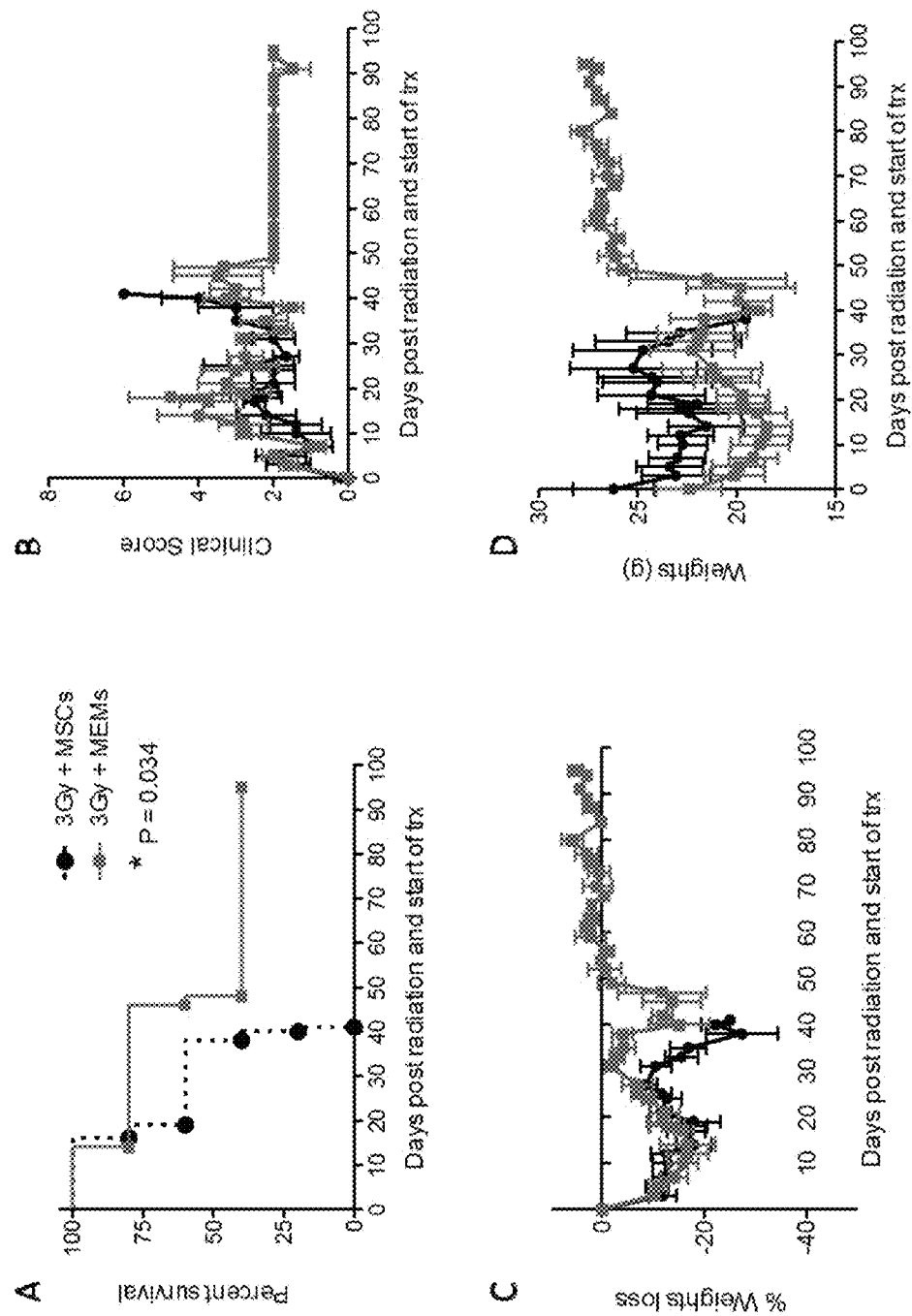
FIGS. 5A-D

FIGS. 6A-B
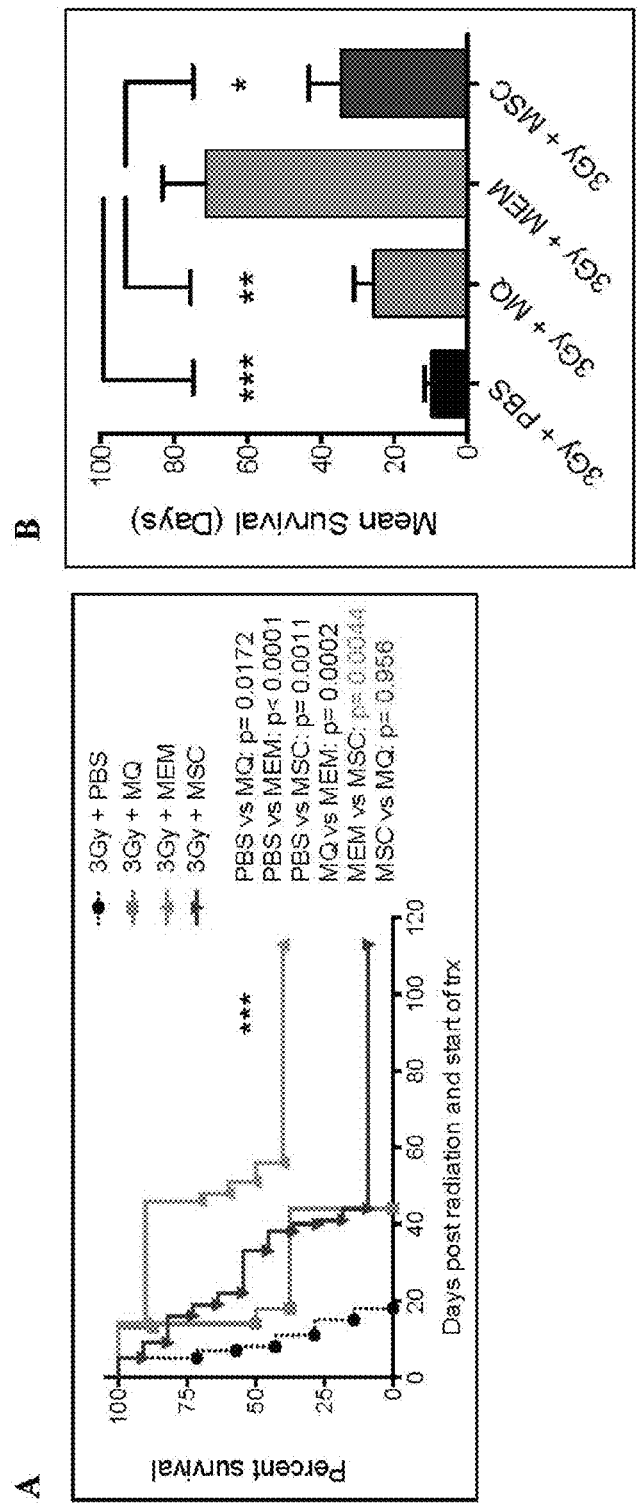

FIGS. 11A-C
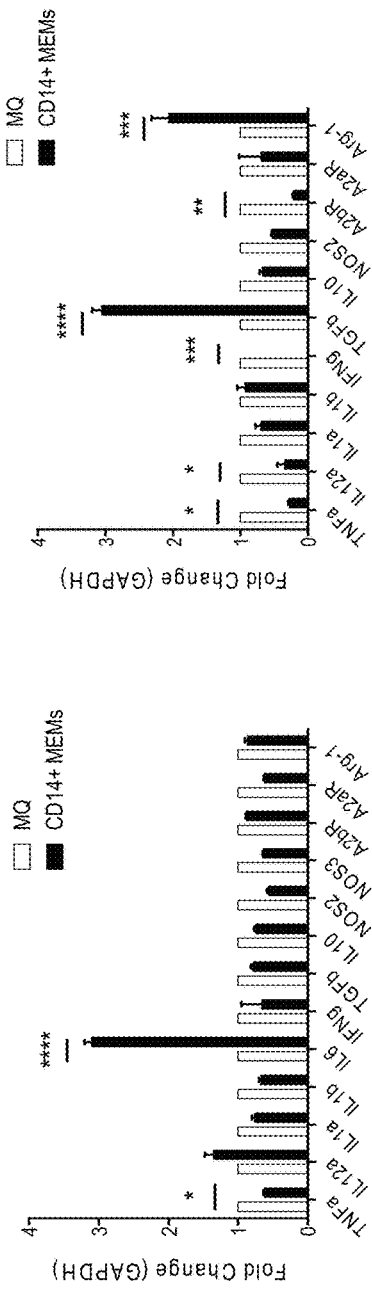

USE OF MESENCHYMAL STEM CELL-EDUCATED MACROPHAGES TO TREAT AND PREVENT GRAFT VERSUS HOST DISEASE AND RADIATION-INDUCED INJURY

CROSS-REFERENCE TO RELATED APPLICATIONS

This application claims priority to U.S. Provisional Application Ser. No. 62/052,672, filed Sep. 19, 2014, which is herein incorporated by reference in its entirety.

STATEMENT REGARDING FEDERALLY SPONSORED RESEARCH

This invention was made with government support under HL081076 awarded by the National Institutes of Health. The government has certain rights in the invention.

BACKGROUND OF THE INVENTION

The present invention relates to methods of using anti-inflammatory macrophages in the treatment and prevention of radiation-induced tissue injury, bone marrow failure, and graft-versus-host-disease.

There is considerable interest in developing therapies that can protect patients who have been exposed to high doses of radiation for either medical purposes, such as for treatment of certain cancers and in preparation for bone marrow transplant (BMT; also known as a hematopoietic stem cell transplant), or accidental trauma, such as from a radiation accident or a terrorist attack. For example, patients receiving an allogeneic hematopoietic stem cell transplant (AlloHSCT), which is a transfusion of hematopoietic stem and progenitor cells, from donor derived bone marrow (BM), mobilized peripheral blood, cord blood or embryonic/pluripotent stem cell derived HSC, into a recipient with a malignancy such as leukemia or non-malignant disorder such as an immunodeficiency, often undergo a pre-transplant radiation-based conditioning regimen. Pre-transplant radiation treatment causes tissue damage in the recipient and increases the risk of development of graft-versus-host disease (GVHD), a condition in which donor cells recognize the recipient's organs as "foreign" and mount an immune response to attack the recipient's own tissue. GVHD is the major cause of morbidity and mortality following AlloHSCT. Because GVHD can be a life threatening complication, it is typically treated with immunosuppressants for weeks to months. The paradox is that GVHD and the current drugs used for treating GVHD, inhibit the function of the donor T cell—simultaneously abrogating anti-tumor benefits and increasing the risk of infections in the recipient. It has been shown that mesenchymal stem cells isolated from BM are effective in treating acute GVHD after allogeneic HSCT. Le Blanc et al., *Lancet* 371:1579-1586 (2008).

In the case of radiation-induced trauma, exposure to high levels of radiation can cause BM failure, leading to anemia, life threatening infections, and high risks of bleeding. While victims exposed to low doses of radiation may spontaneously recover their own immune systems, those victims exposed to myeloablative doses of radiation must urgently receive allogeneic HSCT. Unfortunately coordinating allogeneic HSCT takes weeks to months, while the victim is at high risk of death. If the exposure is serious enough, the victim may even be too ill to undergo allogeneic HSCT. In addition, exposure to high dose radiation can cause damage to non-BM organs, such as lungs and gastrointestinal tract, with a high rate of morbidity and mortality. Organ damage is often the primary limiting factor in delivering higher doses of radiation for treatment of cancer, as exposure of normal tissues surrounding a tumor mass to high dose radiation could cause irreversible damage. Thus, there remains an urgent need for therapies that can be rapidly implemented following systemic or localized radiation exposure to minimize the effects of radiation on the BM, effective therapies for radiation-induced organ damage, to enhance immune recovery, and to prevent development of GVHD if patient receives allogeneic HSCT.

SUMMARY OF THE INVENTION

In a first aspect, provided herein is a method of treating a radiation-induced disorder in a subject having, or at risk of having, a radiation-induced disorder. The method comprising administering to the subject a therapeutically effective amount of human mesenchymal stem cell-educated macrophages (MEMs), thereby treating a disorder in the subject resulting from exposure to ionizing radiation. The ionizing radiation exposure can be a consequence of intentional radiation therapy or accidental radiation exposure. The subject can be exposed to ionizing radiation prior to administering MEMs. The MEMs can be administered to the subject prior to exposure to ionizing radiation. The MEMs can be administered in a pharmaceutical composition comprising MEMs and a pharmaceutically acceptable carrier. The MEMs can be administered intravenously, intratracheally or locally directly into the exposed or damaged organ. The radiation-induced disorder can be acute, subacute, or chronic.

The radiation-induced disorder can be selected from the group consisting of BM failure, radiation pneumonitis, radiation enteritis, radiation enteropathy, radiation enterocolitis, radiation dermatitis, radiation-induced erythema, radiation colitis, radiation proctitis, radiation cystitis, radiation nephritis, radiation esophagitis, radiation pericarditis, radiation-induced cardiac effusion, and radiation-induced cardiac fibrosis. In some cases, the radiation-induced disorder is a lung disorder resulting from thoracic exposure to ionizing radiation. The radiation-induced lung disorder can result in impaired lung function and the method improves the impaired lung function.

In another aspect, provided herein is a method of preventing a radiation-induced injury in a subject. The method can comprise or consist essentially of administering a therapeutically effective amount of MEMs to a subject at risk of developing a radiation-induced injury, whereby the radiation-induced injury is prevented in the subject.

In a further aspect, provided herein is a method of suppressing development of graft versus host disease (GVHD) in a subject in need thereof. The method can comprise or consist essentially of administering to the subject a therapeutically effective amount of human MEMs, where administering suppresses the development of GVHD in the subject. In some cases, the subject has undergone, is undergoing, or will undergo an allogeneic hematopoietic stem cell transplant. The allogeneic hematopoietic stem cell transplant can comprise hematopoietic cells obtained from donor BM, peripheral blood, or umbilical cord blood, or generated from human pluripotent stem cells.

In yet another aspect, provided herein is a method of treating GVHD or a symptom thereof in a subject. The method can comprise or consist essentially of administering to the subject a therapeutically effective amount of human MEMs, where administering treats GVHD or a symptom thereof in the subject.

Also provided herein is a pharmaceutical composition comprising human MEMs and a pharmaceutically acceptable carrier. The pharmaceutical composition can further comprise a pharmaceutically acceptable cryopreservant.

Also provided herein is a kit comprising a pharmaceutical composition as provided herein and instructions for administering the pharmaceutical composition to a human subject. The kit can further comprise one or more pharmaceutical agents selected from the group consisting of a glucocorticoid, an immunosuppressant, an antineoplastic, an antirheumatic, and an anti-inflammatory or immunomodulatory.

Also provided herein is a kit comprising a pharmaceutical composition as provided herein and instructions for administering the composition to a human subject, where the MEMs are provided as a frozen aliquot in the pharmaceutically acceptable cryopreservant. The kit can further comprise one or more pharmaceutical agents selected from the group consisting of a glucocorticoid, an immunosuppressant, an antineoplastic, and an anti-inflammatory or immunomodulatory.

Unless otherwise defined, all technical and scientific terms used herein have the same meaning as commonly understood by one of ordinary skill in the art to which this invention belongs. Although suitable materials and methods for the practice or testing of the present invention are described below, other materials and methods similar or equivalent to those described herein, which are well known in the art, can be used.

Other objectives, advantages and features of the present invention will become apparent from the following specification taken in conjunction with the accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

The present invention will be better understood and features, aspects, and advantages other than those set forth above will become apparent when consideration is given to the following detailed description. Such detailed description makes reference to the following drawings, wherein:

FIGS. 1A-B demonstrate the in vitro phenotype of human macrophages (MQs) and human mesenchymal stem cell-educated macrophages (MEMs). $CD14^+$ monocytes were isolated from PBMCs from a healthy donor and cultured for 7 days in a macrophage medium: IMDM (Iscove's Modified Dulbecco's Medium) supplemented with 10% human serum from type AB blood, 1× Non-essential amino acids, 4 mM L-Glutamine, 1 mM Sodium pyruvate, and 4 µg/ml recombinant human insulin). On last day of culture, half of the MQs were cultured with MSCs at a 10:1 ratio of MSCs:MQs for an additional 3 days. (A) On day 10, cells in both groups were stained for flow cytometry using antibodies specific to CD14 (cell surface marker specific for macrophages) and CD90 (cell surface marker specific for MSCs). (B) Cell surface expression of CD206 (mannose receptor), CD163 (scavenger receptor), CD86 (co-stimulatory molecule), PD-L1 and PD-L2 (both inhibitory molecules) were determined by flow cytometry. Numbers in the plots denote the mean fluorescent intensity (MFI) value for each group with color-matched histograms.

FIGS. 3A-D demonstrate increased survival following administration of MEMs to treat GVHD that was not induced or exacerbated by radiation with MEMs. On day 0, male NSG mice received a dose of human PBMCs ($30 \times 10^6$ in 0.2 ml PBS intravenously (i.v.)) to induce lethal xenogeneic GVHD. On day 51, mice were randomized such that each group started with the same overall GVHD clinical score. Mice received PBS (0.2 ml i.v.) $5 \times 10^5$ MEMs i.v. to treat GVHD. (A) Survival was compared by log rank analysis. Each group had 7 mice. (B) Percent weight loss for mice of (A) is depicted. (C) Overall GVHD score in PBS or MEM-treated groups for days 137 and 147 post-PBMC transplant. (D) Percent weight loss for days 119, 127, 137 and 147 post day 0 of the PBMC transplant. (C and D) data analyzed by two-way ANOVA with Bonferroni multiple comparisons.

FIGS. 4A-C present data demonstrating increased survival of NSG mice treated with MSC-educated Macrophages (MEMs) in a mouse model of GVHD that was induced or exacerbated by radiation exposure. (A) Survival was compared by log rank analysis. PBS group had 5 mice/group. MEM group had 6 mice/group. (B) Percent weight loss from mice in (A) is depicted. (C) Overall GVHD score in PBS or MEM-treated groups. Data analyzed by correlation analysis for graph (C).

FIGS. 5A-D are graphs demonstrating that MEMs increase survival in a non-transplant, non-GVHD lethal radiation injury model incorporating total body irradiation. On day 0, NSG mice received a dose of lethal total body irradiation (3Gy), then 3 hours later were treated with $5 \times 10^5$ MSCs or $5 \times 10^5$ MEMs (by i.v. administration). PBS group had 5 mice/group and MEM group had 6 mice/group. (A) Survival curve compared by log rank analysis. Each group has 5 mice/group. (B) Overall clinical score in MSC or MEM-treated groups. (C) Percent weight loss from mice is depicted. (D) Weight in grams for each group.

FIGS. 6A-B present data demonstrating that treatment of lethal radiation with MEMs improves survival compared to MSCs or macrophages alone. On day 0, NSG mice received total body irradiation (3Gy) followed by (3 hours later) PBS, $5 \times 10^5$ MQs, $5 \times 10^5$ MSCs or $5 \times 10^5$ MEMs treatment (i.v.) PBS group had 7 mice/group, MQ had 8 mice/group, MEM group had 10 mice/group and MSC had 11 mice/group. (A) Survival curve compared by log rank analysis. Survival data shown up to day 113 post irradiation. *=p<0.01. (B) Mean survival in days for each group.* p=0.0003, **p=0.0066, *p=0.02 (Mean±SEM by One way ANOVA of analysis with Bonferroni multiple comparison post test).

FIGS. 11A-C presents gene expression data by RT-PCR in macrophages (MQ) or MEMs derived from peripheral blood (PB) or bone marrow (BM). On day +0 CD14$^+$ monocytes from either PB or BM were isolated, cultured for 7 days in macrophages media (IMDM (Iscove's Modified Dulbecco's Medium) supplemented with 10% human serum from type AB blood, 1× Non-essential amino acids, 4 mM L-Glutamine, 1 mM Sodium pyruvate, and 4 µg/ml recombinant human insulin). On day 7 to day 10, half of the MQs from PB or BM were cultured with MSCs at a 10:1 ratio of MSCs:MQs for an additional 3 days. On day +10, cells were harvested and sorted for CD14+ cells to eliminate the MSCs in the MEMs groups (both from PB or BM-derived MEMs) and RNA was isolated from each group for RT-PCR assessment of gene expression of pro- and anti-inflammatory genes. All RT-PCR was normalized to the housekeeping gene GAPDH and the fold change of expression is depicted. (A) Significant downregulation of the pro-inflammatory cytokine TNFα and a significant increase in IL-6 (important in wound healing and tissue regeneration) expression were observed in bone marrow-derived MEMs (BM-MEMs) compared to BM-MQ. (B) A significant decrease in the pro-inflammatory cytokines TNFα, IL-12 and IFN' and in the adenosine 2b receptor (A2bR) and a significant increase in arginase-1 (Arg-1) (inhibits nitric oxide release and is involved in wound healing) and the anti-inflammatory transforming growth factor-β (TGFβ) were observed in peripheral blood-derived MEMs (PB-MEMs) compared to PB-MQ. NOS3 was undetected in both groups. CT values were undetermined (C) Demonstrates a significant increase in IL-6 expression in both PB- and BM-derived MEMs compared to PB-MQ or BM-MQ, however PB-MEMs show a much higher expression in IL-6 compared to BM-MEMs. Data analyzed by two way ANOVA with Bonferroni's multiple comparison post test (Mean±SEM) (For panels A and B) or with one way ANOVA with Dunn's multiple comparison post test (Mean±SEM) (For panel C). *=p<0.05, =p<0.01, *=p<0.001, ****=p<0.0001.

Figure 2A:
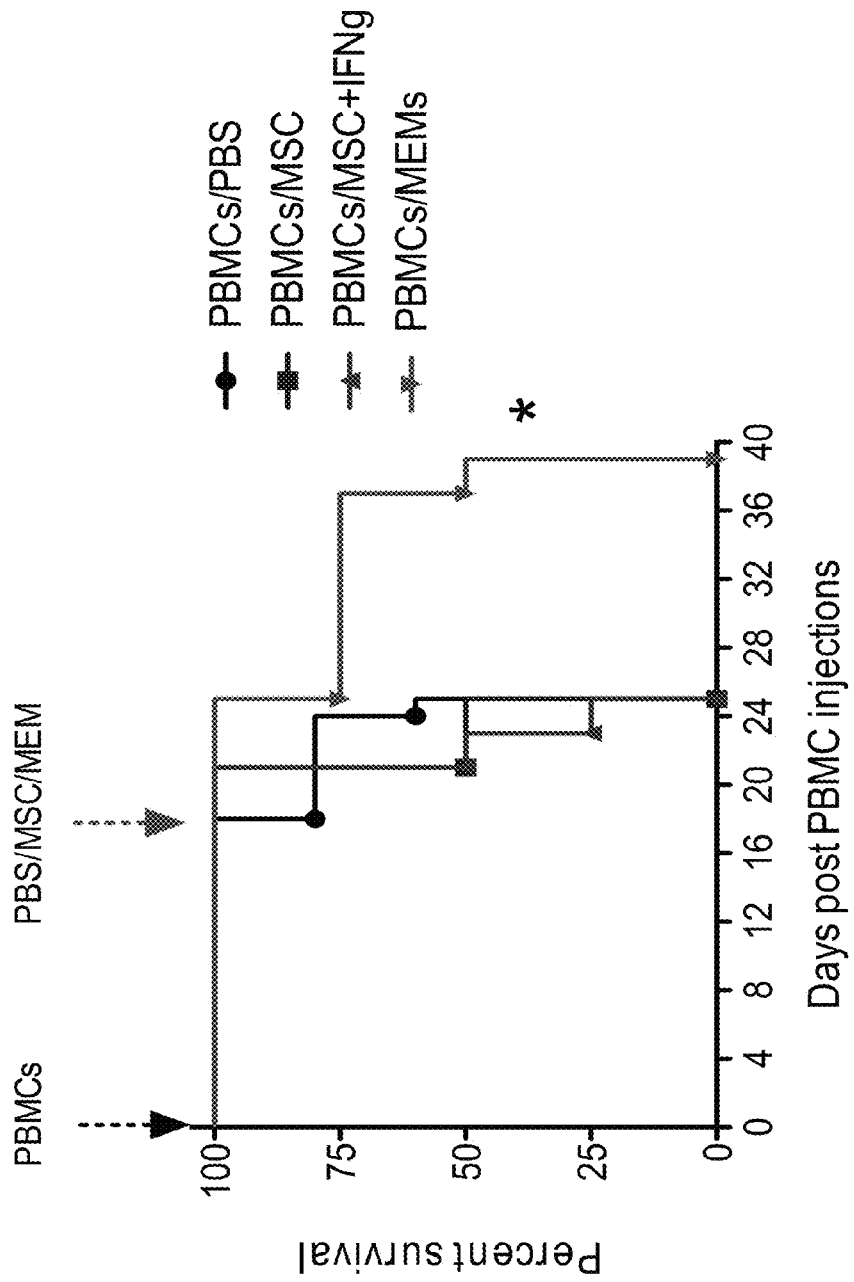
FIG. 2A and FIG. 2B demonstrate increased survival of NSG mice treated with MSC-educated macrophages (MEMs) in a GVHD model (A) without radiation and (B) with radiation. (A) On day 0, NSG mice received a dose of human PBMCs ($30 \times 10^6$ in 0.2 ml PBS intravenously (i.v.)) to induce lethal xenogeneic GVHD, which shares the clinical features of acute GVHD. On day 18, when all of the mice showed clinical evidence of GVHD (based on weight loss, posture, activity, skin and fur texture of the mice), mice were randomized such that each group started with the same overall GVHD score. Mice received PBS (0.2 ml i.v.), $5 \times 10^4$ MSCs, or $5 \times 10^4$ MSCs grown with IFNγ, or $5 \times 10^4$ MEMs i.v. to treat GVHD. Survival was compared by log rank analysis. PBS group had 5 mice/group and MSC or MSC+ IFNγ or MEM groups had 4 mice/group. (B) NSG mice were lethally irradiated with 3Gy on Day+0 and injected intravenously (i.v) with a sublethal dose of human PBMCs ($15 \times 10^6$ in 0.2 ml PBS) to induce a mild acute xenogeneic GVHD. On day +17, when all of the mice showed clinical evidence of GVHD, mice were randomized to receive macrophages (Mac) or MEMs i.v ($5 \times 10^5$ cells in 0.2 ml PBS per mouse) to treat GVHD. On Day+52, mice were given a lethal boost of PBMCs ($15 \times 10^6$) and another dose of either macrophages (Mac) or MEMs as treatment ($4 \times 10^5$ in 0.2 ml PBS i.v). All mice were followed for survival.
Figure 2B:
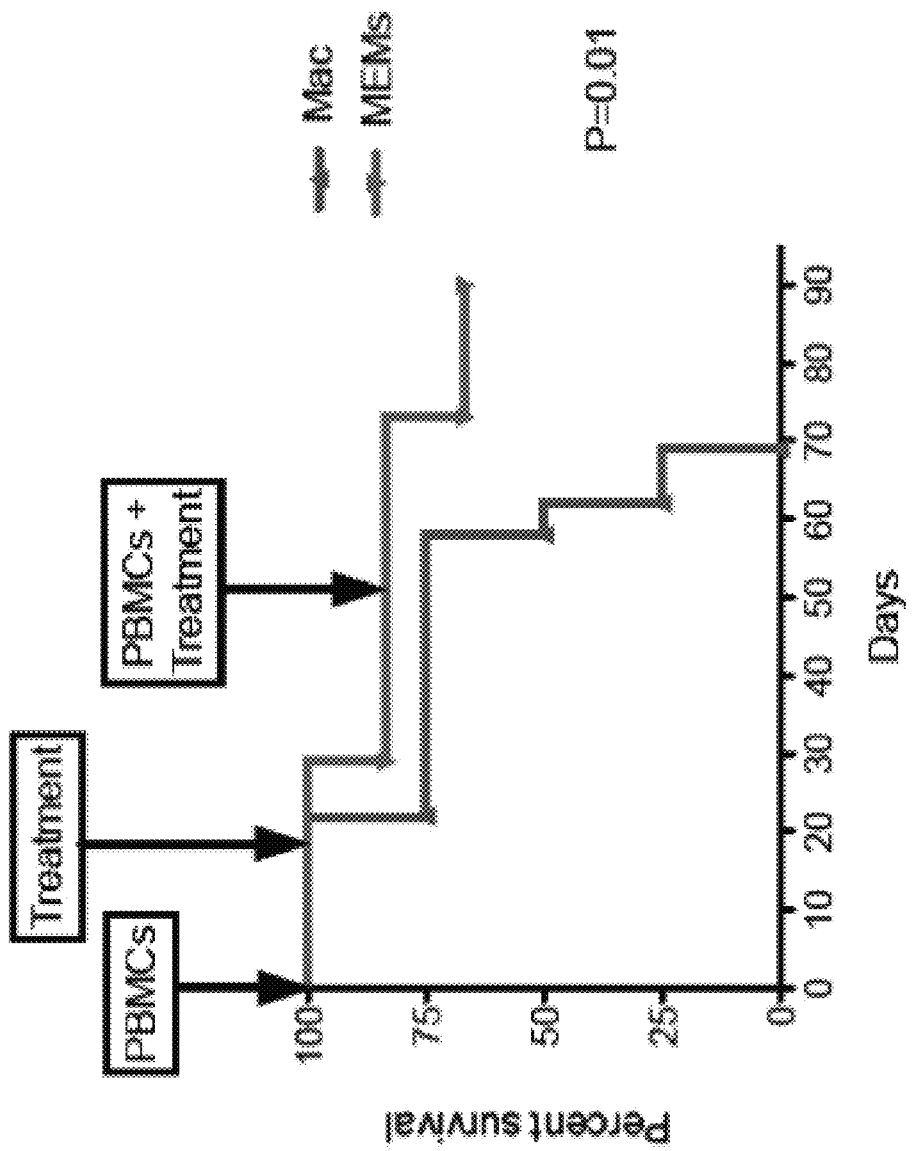

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION OF THE INVENTION

The present invention is based at least in part on the Inventors' discovery that mesenchymal stem cell-educated macrophages (MEMs) have potent tissue regenerative properties that can minimize tissue damage from radiation and increase survival in clinically significant ways. As demonstrated in a relevant pre-clinical model, the therapeutic methods provided herein are superior to other forms of cellular therapy for treating and preventing radiation-induced morbidity and mortality, GVHD, and other conditions associated with aberrant, uncontrolled, or inappropriate inflammation.

Methods

Accordingly, in a first aspect, the present invention provides methods of treating or preventing a radiation-induced disorder, bone marrow failure, a condition associated with aberrant, uncontrolled, or inappropriate inflammation, or graft-versus-host disease (GVHD) in a subject in need thereof, where the methods comprise administering to the subject effective amounts of human mesenchymal stem cell (MSC)-educated macrophages (MEMs) whereby the radiation-induced disorder, bone marrow failure, conditions associated with aberrant inflammation, or GVHD is treated or prevented.

As used herein, the term "mesenchymal stem cell (MSC)-educated macrophages" (MEM) refers to a type of alternatively activated macrophages having anti-inflammatory properties, characterized by high levels of expression of the anti-inflammatory/tissue regenerative cytokines IL-10 and IL-6, and low levels of expression of the pro-inflammatory cytokines IL-12 and TNF-α. See U.S. Pat. No. 8,647,678; incorporated herein by reference. MEMs are generated by co-culturing CD14$^+$ cells with mesenchymal stem cells (MSCs). MSCs are also referred to in the literature as mesenchymal stromal cells or mesenchymal stromal/stem cells. As used herein, a "CD14$^+$ cell" is a monocyte which, after about 1 to about 7 days (e.g., about 1, 2, 3, 4, 5, 6, 7 days) of culture in vitro, gives rise to macrophages. As used herein, the term "macrophage" refers to a mononuclear phagocyte characterized by the expression of CD14 and lack of expression of dendritic cell markers. Macrophages are negative for expression of CD90 (a marker of MSCs) and have lower surface expression levels of the mannose receptor CD206 and the scavenger receptor CD163. Monocytes are mononuclear leukocytes that can differentiate into macrophages.

MEMs appropriate for use according to the methods provided herein are CD14$^+$/CD90$^-$/CD206$^+$/CD163$^+$ and include those described in U.S. Pat. No. 8,647,678, which is incorporated herein by reference as if set forth in its entirety. In exemplary embodiments, MEMs for use according to a method of the invention are obtained by co-culturing CD14$^+$ cells derived from bone marrow or peripheral blood of a human donor with human mesenchymal stem cells. Macrophages (MQs) and MEMs both express CD14, but MEMs acquire a tissue regenerative and immunomodulatory phenotype by secreting IL10 and upregulating surface expression of CD206 and CD163 (markers known to be highly expressed by alternatively activated macrophages stimulated by IL-13 or IL-4). Unlike classical "alternatively activated macrophages" or "AAMs," which express high levels of IL10 and low levels of IL-6, IL-12, and TNFα, MEMs express high levels of IL-10 and IL-6 and low levels of IL-12 and TNFα. Also, there is no evidence to date that AAMs express programmed death ligand-1 or 2 (PD-L1 and PD-L2), which are inhibitory molecules that bind to PD-1 (programmed death-1) on T cells leading to the suppression of T cell activation and proliferation. Without being bound to any theory or mechanism of action, MEMs may inhibit donor T cell activation and proliferation by acting on PD-L1 or PD-L2, and MEMs may participate in tissue regeneration by expression of IL-10 and IL-6. Other markers that can be used to identify MEMs appropriate for use according to the methods provided herein include Arginase-1 (Arg-1) and Transforming Growth Factor Beta (TGFβ), both of which are anti-inflammatory molecules.

In some cases, MEMs are obtained using MSCs and macrophages co-cultured and passaged as described in Example 1. MSCs used to obtain MEMs can be obtained from any suitable source. MSCs can be isolated from virtually every tissue and organ including, but not limited to, bone marrow, umbilical cord blood, peripheral blood, pancreas, heart, adipose tissue, lung, liver, skin, kidney, and thyroid gland. MSCs can also be produced from pluripotent cells, such as embryonic stem cells and induced pluripotent cells. Trivedi and Hematti, *Exp. Hematol.* 36(3):350-359 (2008). MEMs useful for the methods provided herein can be sorted from the MSC/MQ co-culture, or can be administered as a combined product without undergoing a sorting, separation, or purification step. In some cases, one or more cell mobilization agents can be used to mobilize hematopoietic cells from the hematopoietic organs of the body, such as bone marrow, liver, or spleen, into the peripheral circulation for harvesting of CD14$^+$ cells. Exemplary cell mobilization agents include, without limitation, Granulocyte colony-stimulating factor (G-CSF), pegfilgrastim (a PEGylated form of the recombinant human GCSF analog filgrastim), stem cell factor (SCF), thrombopoietin, Granulocyte-macrophage colony-stimulating factor (GM-CSF), and Macrophage inflammatory protein-1α (MIP1α/CCL3).

MSCs and macrophages used to obtain MEMs can be allogeneic, syngeneic, or autologous with respect to each other. As used herein, "allogeneic" refers to cells or tissues taken from different individuals of the same species that are not genetically identical. As used herein, "syngeneic" refers to cells or tissues that are genetically identical or closely related, including pluripotent stem cells. As used herein, "autologous" refers to cells or tissues taken from the same individual that are genetically identical, including pluripotent stem cells.

In some cases, MEMs are obtained by culturing macrophages in the presence of not intact MSCs but microvesicles derived from MSCs such as exosomes. As used herein, "exosomes" refer to small lipid vesicles that are released by a variety of cell types including mesenchymal stem cells. Exosomes are generated by inward or reverse budding, resulting in particles that contain cytosol and exposed extracellular domains of certain membrane-associated proteins (Stoorvogel et al., *Traffic* 3:321-330 (2002)). Methods of preparing exosomes from cells are known in the art. See, for example, Raposo et al., *J. Exp. Med.* 183:1161 (1996). Preferably, exosomes are recovered from conditioned culture medium of MSCs for example, but not by way of limitation, by centrifugation. For use according to a method provided herein, exosomes are co-cultured with macrophages as described with respect to mesenchymal stem cells in Example 1. In some cases, exosomes are subjected to additional purification steps prior to use in co-culture to obtain MEMs. Exosomes from MSCs could be added in a single dose or repeated doses to MQ cultures to generate MEMs. Exosomes could be derived fresh or be used from previously made frozen aliquots that had been kept as a composition, thawed, and added in a single dose or repeated doses to MQ cultures to generate MEMs.

As used herein, the terms "treat" and "treating" refer to both therapeutic and prophylactic or preventive measures, wherein the object is to prevent or slow down (lessen) an undesired physiological change or pathological disorder resulting from exposure to ionizing radiation. For purposes of this invention, treating a radiation-induced disorder includes, without limitation, alleviating one or more clinical indications, decreasing inflammation, reducing the severity of one or more clinical indications of a radiation-induced or radiation-associated condition, diminishing the extent of the condition, stabilizing the subject's disease state (i.e., not worsening), delay or slowing, halting, or reversing radiation-induced injury progression, and bringing about partial or complete remission. Treating a radiation-induced disorder also includes prolonging survival by days, weeks, months, or years as compared to prognosis if treated according to standard medical practice not incorporating treatment with MEMs. Subjects in need of treatment can include those already having or diagnosed with a radiation-induced injury or condition associated with aberrant inflammation as well as those prone to, likely to develop, or suspected of having a radiation-induced injury (e.g., acute radiation syndrome) or a condition associated with aberrant inflammation. Pre-treating a radiation-induced disorder according to a method of the present invention includes initiating the administration of a therapeutic (e.g., human MEMs) at a time prior to the appearance or existence of the radiation-induced disorder, or prior to the exposure of a subject to ionizing radiation. Pre-treating the disorder is particularly applicable to subjects at risk of having a radiation-induced disorder. As used herein, the terms "prevent" and "preventing" refer to prophylactic or preventive measures intended to inhibit undesirable physiological changes or the development of a disorder or condition resulting from exposure to ionizing radiation. In exemplary embodiments, preventing a radiation-induced disorder comprises initiating the administration of a therapeutic (e.g., human MEMs) at a time prior to the appearance or existence of the radiation-induced disorder such that the radiation-induced disorder, or its symptoms, pathological features, consequences, or adverse effects do not occur. In such cases, a method of the invention for preventing a radiation-induced disorder comprises administering MEMs to a subject in need thereof prior to exposure of the subject to ionizing radiation.

According to the methods of the present invention, MEMs are administered to a subject in need of thereof. Subjects in need of treatment include those already having or diagnosed with a radiation-induced injury, bone marrow failure, a condition associated with aberrant, uncontrolled, or inappropriate inflammation, or a pathological symptom or feature associated with radiation-induced disorders. Subjects in need thereof also include those subjects prone to, likely to develop, or suspected of having a radiation-induced injury (e.g., acute radiation syndrome), bone marrow failure, a condition associated with aberrant inflammation, or a pathological symptom or feature associated with radiation-induced disorders. As used herein, the terms "subject" or "patient" are used interchangeably and can encompass any vertebrate including, without limitation, humans, mammals, reptiles, amphibians, and fish. However, advantageously, the subject or patient is a mammal such as a human, or a mammal such as a domesticated mammal, e.g., dog, cat, horse, and the like, or livestock, e.g., cow, sheep, pig, and the like. In exemplary embodiments, the subject is a human. As used herein, the phrase "in need thereof" indicates the state of the subject, wherein therapeutic or preventative measures are desirable. Such a state can include, but is not limited to, subjects having an illness or tissue injury caused by or associated with radiation exposure (e.g., bone marrow failure).

As used herein, the term "radiation-induced disorder" refers to any disorder, disease, or pathological condition that occurs as a result of, or is induced by, whole body or localized exposure of a subject to ionizing radiation of sufficient intensity and duration to bring about an undesirable effect, for example, undesirable tissue damage. Sources of radiation exposure include, without limitation, radiation therapy (e.g., localized radiation exposure to a tissue or organ), unintended exposure to ionizing radiation (e.g., nuclear accident, act of terrorism), and improper or unauthorized disposal of radioactive material.

"Radiation-induced disorders" also include various forms of systemic or localized tissue damage caused by or associated with radiation exposure either to the whole body or localized to a region of the body (e.g., lung, kidney, bone). Radiation-induced disorders include bone marrow failure, bone marrow toxic injury, and acute radiation syndrome (ARS). ARS is generally associated with full body exposure to high levels of radiation or levels sufficient to penetrate and irradiate internal organs. In exemplary embodiments, a radiation-induced disorder appropriate for methods of the present invention is one associated with or characterized, at least in part, by bone marrow failure, infection, bleeding, tissue damage, organ failure, and increased susceptibility to graft-versus-host disease (GVHD). As used herein, "bone marrow failure" refers to the pathologic process where bone marrow that has been damaged by radiation therapy, chemotherapy, disease or toxins is not able to be restored to normal and, therefore, fails to produce sufficient blood cells to maintain proper hematopoiesis in the mammal. In some cases, bone marrow failure is a result of certain disease states or is induced by the use of certain treatment modalities, such as aggressive chemotherapy and/or radiation therapy.

Conditions associated with aberrant, uncontrolled, or inappropriate inflammation include, but are not limited to, arthritis, multiple sclerosis and other autoimmune disorders, cardiovascular disease, atherosclerosis, neurodegeneration, cancer, cytokine release syndrome (CRS), and other disorders associated with cytokine storm such as adult respiratory distress syndrome (ARDS), severe acute respiratory syndrome (SARS), sepsis, influenza, hemophagocytic lymphohistiocytosis (HLH) (also known as macrophage activation syndrome (MAS)), and systemic inflammatory response syndrome (SIRS). CRS is a rapid and massive release of cytokines into the bloodstream which can lead to high fevers and cardiac dysfunction, and is frequently observed following administration of immunotherapeutics (e.g., therapeutic mAb infusions) and following adoptive T-cell therapies (e.g., administration of T-cells engineered to express CARs). While immunosuppression can potentially reverse a cytokine storm and return cytokines to normal levels, it can limit the efficacy of the immunotherapy. Advantageously, the methods provided herein improve the chance for the subject to receive therapeutic benefit from an immunotherapy while minimizing the risk for life threatening complications of CRS and other cytokine-associated toxicities.

As used herein, the term "autoimmune disease" refers to any disease which results in an aberrant immune response caused by a failure of the body to distinguish self from non-self Typically, the autoimmune disease is selected from the group including but not limited to; Acute disseminated encephalomyelitis (ADEM); Addison's disease; Alopecia areata; Ankylosing spondylitis; Antiphospholipid antibody syndrome (APS); Autoimmune hemolytic anemia; Autoimmune hepatitis; Autoimmune inner ear disease; Bullous pemphigoid; Coeliac disease; Chagas disease; Chronic obstructive pulmonary disease; Crohns Disease; Dermatomyositis; Diabetes mellitus type 1; Endometriosis; Goodpasture's syndrome; Graves' disease; Guillain-Barré syndrome (GBS); Hashimoto's disease; Hidradenitis suppurativa; Kawasaki disease; IgA nephropathy; Idiopathic thrombocytopenic purpura; Interstitial cystitis; Lupus erythematosus; Mixed Connective Tissue Disease; Morphea; Multiple sclerosis (MS); Myasthenia gravis; Narcolepsy; Neuromyotonia; Pemphigus vulgaris; Pernicious anaemia; Psoriasis; Psoriatic Arthritis; Polymyositis; Primary biliary cirrhosis; Rheumatoid arthritis; Schizophrenia; Scleroderma; Sjögren's syndrome; Stiff person syndrome; Temporal arteritis (also known as "giant cell arteritis"); Ulcerative Colitis; Vasculitis; Vitiligo; Wegener's granulomatosis.

For the methods provided herein, the neurodegenerative disease is selected from the group consisting of: a motor neuron disease (e.g., amyotrophic lateral sclerosis (ALS)) or a variant thereof including primary lateral sclerosis and spinal muscular atrophy; prion disease; Huntington's disease; Parkinson's disease; Parkinson-plus syndromes (tauopathies and synucleinopathies); Chromosome 17 dementias; Alzheimer's disease; Multiple sclerosis (MS);

hereditary neuropathies; and diseases involving corticobasal degeneration (CBD) or corticobasal ganglionic degeneration (CBGD).

As used herein, the term "cardiovascular disease" refers to a cardiovascular disease selected from the group comprising coronary heart disease, cardiomyopathy (for example, coronary artery disease, ischemic cardiomyopathy, hypertensive cardiomyopathy, valvular cardiomyopathy, inflammatory cardiomyopathy (such as endocraditis, inflammatory cardiomegaly, and myocarditis)), cardiovascular disease (for example, atherosclerosis), and ischemic heart disease.

With respect to radiation-induced injury, an amount of ionizing radiation exposure resulting in radiation-induced conditions appropriate for treatment or prevention according to a method provided herein is generally between minimal and maximal tolerance doses. The minimal tolerance dose ($T/D_{5/5}$) is the dose that when administered to a given patient population under a standard set of treatment conditions, results in a rate of severe complications of 5% or less within 5 years of treatment. The maximal tolerance dose ($T/D_{50/5}$) is the dose that when administered to a given patient population under a standard set of treatment conditions, results in a rate of severe complications of 50% or less within 5 years of treatment. $T/D_{5/5}$ and $T/D_{50/5}$ have been established for many conditions and are well-known (see, e.g., Rubin et al. (Eds) Radiation Biology and Radiation Pathology Syllabus, set RT 1 Radiation Oncology, Chicago, American College of Radiology, 1975). The minimal tolerance dose and maximal tolerance dose have been established with respect to therapeutic radiation treatments but are applicable as well for determining the range of radiation exposure suitable for causing the radiation-induced disorders resulting from exposure to radiation from other sources (e.g., occupational or environmental exposures).

Radiation is quantitated on the basis of the amount of radiation absorbed by the body, not based on the amount of radiation produced by the source. A rad (radiation absorbed dose) is 100 ergs of energy per gram of tissue; a gray (Gy) is 100 rad. Radiation dose can be measured by placing detectors on the body surface or by calculating the dose based on radiating phantoms that resemble human form and substance. Radiation dose has three components: total absorbed dose, number of fractions, and time. Most teletherapy radiation therapy programs are fractionated, being delivered in fractions periodically over time, typically once a day, 5 days a week, in 150-200 cGy fractions, generally applied to limited target areas of the body. The total dose delivered in radiation therapy will vary depending on the nature and severity of the condition being treated. For curative cases, the absorbed dose typically will range from 20-80 Gy. For preventative cases, doses are typically around 45-60 Gy and are applied in fractions of about 1.8-2 Gy per day. When used for radiation therapy, ionizing radiation is usually provided over a period of time or until a particular amount of radiation exposure has been reached by the target area of the subject. Sources of ionizing radiation include electrons, X-rays, gamma rays, and atomic ions. Exposure of a subject to ionizing radiation may be due to a medical procedure including, but not limited to, radiation therapy to treat certain malignant conditions, e.g., lung or breast cancer; medical procedures such as diagnostic X-rays; or procedures involving administration of nuclear medicines. Exposure to ionizing radiation also can result from a nuclear accident or from known or suspected occupational or environmental sources, e.g., various consumer products including, but not limited to, tobacco, combustible fuels, smoke detectors, and building materials.

Radiation-induced disorders appropriate for treatment with methods of the present invention can result from exposure to ionizing radiation in the course of radiation therapy. As used herein, the term "radiation therapy" refers to the medical use of high-energy ionizing radiation to shrink tumors, to control malignant cell growth, or, where appropriate, to treat non-malignant conditions such as thyroid eye disease or pigmented villonodular synovitis. X-rays, gamma rays, and charged particles are types of radiation used for radiation therapy. The radiation may be delivered by a machine outside the body (external-beam radiation therapy, also called teletherapy), or it may come from encapsulated radioactive material implanted directly into or adjacent to tumor tissues in the body near cancer cells (internal radiation therapy, also called brachytherapy). Systemic radiation therapy uses radioactive substances, such as radioactive iodine, that travel in the blood and are targeted in some fashion to the cancer cells. Teletherapy is the most common form of radiation therapy. About half of all cancer patients receive some type of radiation therapy sometime during the course of their treatment.

Radiation-induced disorders in different tissues and organs generally follow a similar course after exposure to ionizing radiation, particularly as a consequence of radiation therapy. Depending on the dose of ionizing radiation to which the subject is exposed, the subject experiences an acute response phase that generally occurs days to weeks following exposure to ionizing radiation. The acute response phase typically involves inflammatory components, is generally self-limiting, and, in some patients, can to resolve within a relatively short time. Depending on the dose of ionizing radiation to which the subject is exposed, the acute phase may be followed by a chronic phase, generally beginning one or more months after exposure. The chronic phase is often characterized by extensive tissue remodeling and fibrosis. Results presented herein suggest that effective treatment of the acute response may mitigate or attenuate the chronic phase. Cancers or tumors that occasionally develop, often many years later, at or near the site of radiation exposure are not intended to be included among the disorders suitable for treatment in the method of the present invention. Radiation-induced disorders, particularly those resulting from radiation therapy, are well known and have been observed in a variety of tissues and organs. The radiation-induced disorder is not the intended result of the radiation therapy but rather is an unintended, and undesirable, side effect of the exposure of various organs, tissues and body parts to the ionizing radiation used in radiation therapy. The radiation-induced disorder can be a disorder induced by irradiation of any, or multiple, body parts, organs or tissues of the subject, including but not limited to bone marrow, lung, heart, bladder, gastrointestinal tract, large intestine, small intestine, stomach, esophagus, skin, ovaries, testes, urogenital system, kidney, head, neck, pancreas, liver, brain, spinal cord, prostate, vasculature, and muscle. In various aspects the radiation-induced disorder can be, but is not limited to one or more of bone marrow failure, radiation pneumonitis, radiation enteritis, radiation enteropathy, radiation enterocolitis, radiation dermatitis, radiation-induced erythema, radiation colitis, radiation proctitis, radiation cystitis, radiation nephritis, radiation esophagitis, radiation pericarditis, radiation-induced cardiac effusion, and radiation-induced cardiac fibrosis. All of these disorders are well-known and readily identifiable by competent medical practitioners.

In particular embodiments, the present invention provides methods for treating or preventing a radiation-induced lung disorder. As used herein, the term "radiation-induced lung disorder" refers to a lung disorder resulting from thoracic exposure to ionizing radiation, meaning exposure of at least the thorax of the subject to a source of ionizing radiation. In particular embodiments, the radiation-induced lung disorder is radiation pneumonitis. The present invention also provides methods and articles of manufacture useful for pretreating a subject that will have or is at increased risk of having thoracic exposure to ionizing radiation, thereby preventing or reducing the severity of any subsequent radiation-induced lung disorder. Subjects having a radiation-induced lung disorder (e.g., radiation pneumonitis) typically present with a nonproductive cough, shortness of breath, and low-grade fever. Upon evaluation, subjects are found to have reduced total lung volume, residual volume, and vital capacity, but unrestricted air flow into and out of the lungs. Diagnosis of a radiation-induced lung disorder is based on symptoms including dyspnea (i.e., the subjective symptom or uncomfortable awareness of breathlessness), nonproductive cough, and low-grade fever; and generally involves blood tests, e.g., measurement of partial oxygen saturation of the blood; pulmonary function tests, e.g., measurement of total lung volume, residual volume, and vital capacity; and computed tomography (CT) scans of the thorax, e.g., to measure lung density and monitor lung remodeling.

In some cases, a method of treating or preventing a radiation-induced injury comprises administering a pharmaceutical composition comprising a therapeutically effective amount of MEMs as a therapeutic agent (i.e., for therapeutic applications). As used herein, the term "pharmaceutical composition" refers to a chemical or biological composition suitable for administration to a mammal Examples of compositions appropriate for such therapeutic applications include preparations for parenteral, subcutaneous, transdermal, intradermal, intramuscular, intracoronarial, intramyocardial, intraperitoneal, intravenous (e.g., injectable), or intratracheal administration, such as sterile suspensions, emulsions, and aerosols. Intratracheal administration can involve contacting or exposing lung tissue, e.g., pulmonary alveoli, to a pharmaceutical composition comprising a therapeutically effective amount of MEMs. In some cases, pharmaceutical compositions appropriate for therapeutic applications may be in admixture with one or more pharmaceutically acceptable excipients, diluents, or carriers such as sterile water, physiological saline, glucose or the like. For example, MEMs described herein can be administered to a subject as a pharmaceutical composition comprising a saline solution.

Formulations may be designed or intended for oral, rectal, nasal, topical or transmucosal (including buccal, sublingual, ocular, vaginal and rectal) and parenteral (including subcutaneous, intramuscular, intravenous, intradermal, intraperitoneal, intrathecal, intraocular and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology,* eds. J. Swarbrick and J. C. Boylan, 1988-1999, Marcel Dekker, New York).

The preferred route may vary with, for example, the subject's pathological condition or weight or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some cases, MEMs may be optionally administered in combination with one or more active agents. Such active agents include anti-inflammatory, anti-cytokine, analgesic, antipyretic, antibiotic, and antiviral agents, as well as growth factors and agonists, antagonists, and modulators of immunoregulatory agents (e.g., TNF-$\alpha$, IL-2, IL-4, IL-6, IL-10, IL-12, IL-13, IL-18, IFN-$\alpha$, IFN-$\gamma$, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Any suitable combination of such active agents is also contemplated. When administered in combination with one or more active agents, MEMs can be administered either simultaneously or sequentially with other active agents. For example, victims of acute radiation injury may simultaneously receive MEMs and one or more growth factors such as granulocyte colony stimulating factor (G-CSF), granulocyte-monocyte colony stimulating factor (GM-CSF), erythropoietin, or thrombopoietin agonists for a length of time or according to a dosage regimen sufficient to support hematopoietic recovery and to treat, alleviate, or lessen the severity of radiation-induced tissue damage.

In some embodiments, MEMs are administered to a subject in need thereof using an infusion, topical application, surgical transplantation, or implantation. Topical administration can include application of MEMs to a skin lesion resulting from GVHD or radiation-induced burn. In exemplary embodiments, administration is systemic. In such cases, MEMs can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions comprising human MSC-educated macrophages are cryopreserved prior to administration.

Therapeutically effective amounts of MEMs are administered to a subject in need thereof. An effective dose or amount is an amount sufficient to effect a beneficial or desired clinical result. With regard to methods of the present invention, the effective dose or amount, which can be administered in one or more administrations, is the amount of human MEMs sufficient to elicit a therapeutic effect in a subject to whom the cells are administered. In some cases, an effective dose of MEMs is about $1 \times 10^6$ cells/kilogram to about $10 \times 10^6$ cells/kilogram of body weight of the recipient. Effective amounts will be affected by various factors which modify the action of the cells upon administration and the subject's biological response to the cells, e.g., level of radiation exposure, type of damaged tissue, the patient's age, sex, and diet, the severity of inflammation, time of administration, and other clinical factors.

Therapeutically effective amounts for administration to a human subject can be determined in animal tests and any art acceptable methods for scaling an amount determined to be effective for an animal for human administration. For example, an amount can be initially measured to be effective in an animal model (e.g., to achieve a beneficial or desired clinical result). The amount obtained from the animal model can be used in formulating an effective amount for humans by using conversion factors known in the art. The effective amount obtained in one animal model can also be converted for another animal by using suitable conversion factors such as, for example, body surface area factors.

It is to be understood that, for any particular subject, specific dosage regimes should be adjusted over time according to the individual need and the professional judgment of the person administering or supervising the administration of the MEMs. For example, a MEM dosage for a particular subject radiation-induced lung disorder can be increased if the lower dose does not elicit a detectable or sufficient improvement in lung function. Conversely, the dosage can be decreased if the radiation-induced lung disorder is treated or eliminated.

In some cases, therapeutically effective amounts of MEMs can be determined by, for example, measuring the effects of a therapeutic in a subject by incrementally increasing the dosage until the desired symptomatic relief level is achieved. A continuing or repeated dose regimen can also be used to achieve or maintain the desired result. Any other techniques known in the art can be used as well in determining the effective amount range. Of course, the specific effective amount will vary with such factors as the particular condition being treated, the physical condition of the subject, the type of animal being treated, the duration of the treatment, and the nature of any concurrent therapy.

Following administration of MEMs to an individual subject afflicted by, prone to, or likely to develop a radiation-induced injury, graft-versus-host disease, or other condition associated with aberrant inflammation, the subject is observed and assessed for a positive or negative change in clinical symptoms or features of the disease or condition. For example, for methods of treating radiation-induced lung injury in a subject, positive or negative changes in the subject's lung function during or following treatment may be determined by any measure known to those of skill in the art including, without limitation, measuring blood gas parameters (e.g., partial arterial pressure of oxygen or percent oxygen saturation of blood) and measuring lung volume parameters.

In any of the methods of the present invention, the donor and the recipient of the MEMs can be a single individual or different individuals, for example, allogeneic or xenogeneic individuals. As used herein, the term "allogeneic" refers to something that is genetically different although belonging to or obtained from the same species (e.g., allogeneic tissue grafts or organ transplants).

According to a method of the invention, MSCs are obtained from a subject and passaged as described in Example 1. MSCs used to obtain MEMs can be obtained from any suitable source. MSCs can be isolated from virtually every tissue and organ including, but not limited to, bone marrow, umbilical cord blood, peripheral blood (e.g., mobilized peripheral blood), pancreas, heart, adipose tissue, lung, liver, skin, kidney, and thyroid gland. MSCs can also be produced from pluripotent cells, such as embryonic stem cells and induced pluripotent cells. Trivedi and Hematti, *Exp. Hematol.* 36(3):350-359 (2008). MSCs and macrophages used to obtain MEMs can be allogeneic, syngeneic, or autologous with respect to each other. As used herein, "allogeneic" refers to cells or tissues taken from different individuals of the same species that are not genetically identical. As used herein, "syngeneic" refers to cells or tissues that are genetically identical or closely related. As used herein, "autologous" refers to cells or tissues taken from the same individual that are genetically identical.

Administration to the subject can be by local or systemic injection or by topical application. In some cases, the subject is observed or assessed with regard to tissue maintenance, tissue repair or function, or overall condition.

In another aspect, the present invention provides a method of treating or preventing GVHD in a subject in need thereof. GVHD can develop in various clinical settings when tissues containing T cells (blood products, bone marrow, and solid organs) are transplanted from one donor to a recipient who is unable to eliminate donor T cells. Patients whose immune systems are suppressed and are disparate (allogeneic) at multiple human leukocyte antigens from the donor T cells are at particularly high risk for GVHD. For review, see Ferrara et al., *Lancet* 373:1550-1561 (2009). Clinical manifestations of acute GVHD can occur in the skin, gastrointestinal (GI) tract, liver, and lungs, while chronic GVHD typically manifests in the skin, mouth, eyes, muscle, GI tract, liver, lungs, kidneys, heart, and bone marrow. Clinical manifestations of acute GVHD include, without limitation, fever, rash, diarrhea, intestinal bleeding, cramping abdominal pain, anorexia, jaundice, and dyspepsia. With respect to chronic GVHD, ocular clinical manifestations can include burning, irritation, photophobia, and pain due to a lack of tear secretion. Other clinical manifestations of chronic GVHD include, without limitation, obstructive lung disease characterized by wheezing, dyspnea, and/or chronic cough, dry-mouth, neuropathic pain, muscle cramps, stiffening of joints, rash, and abdominal pain.

The pathophysiology of GVHD is complex, but can be classified into three distinct phases: (1) a cytokine storm whereby the conditioning regimen (chemotherapy and/or radiation) causes tissue damage, causing translocation of bacteria across epithelial barriers and release of host antigens from damaged epithelium, (2) an afferent arm where host antigen presenting cells (APCs) prime donor T cells against antigens on the tumor and host, and (3) an efferent arm, where the activated donor T cells proliferate and attack their antigen-bearing targets (Ferrara et al., *The Lancet.* 2009; 373(9674):1550-1561). In the efferent arm, factors that mediate tissue damage (e.g., TNFα, IL-1, IL-2, cytotoxic T cells, Natural Killer cells) promote inflammation and trigger necrosis and apoptosis in host tissues. Conventional GVHD therapeutics are phase non-specific or block the efferent arm, via the T cells, thus also inhibiting the graft-versus-leukemia (GVL) effect. Acute GVHD can affect the skin, liver and gastrointestinal (GI) tract, and the current grading system (grades I-IV) for acute GVHD is based upon the extent of target organ involvement (Przepiorka et al., *Bone Marrow Transplant.* 1995; 15:825-828).

Any type of GVHD, whether preceded or exacerbated by radiation or not, can be treated, suppressed, or prevented by a method of the present invention. GVHD that can be treated by methods of the present invention includes acute GVHD and chronic GVHD. Therapeutic methods for GVHD of the present invention are effective against GVHD following hematopoietic stem cell transplantation, such as GVHD following peripheral blood stem cell transplantation (e.g., allogeneic peripheral blood stem cell transplantation), GVHD following bone marrow transplantation (e.g., allogeneic bone marrow transplantation), GVHD following umbilical cord blood transplantation (e.g., allogeneic umbilical cord blood transplantation), GVHD following blood transfusion (transfusion-associated GVHD), or GVHD following solid organ transplantation. In exemplary embodiments, MEMs are administered to a mammalian subject (preferably, a human subject), whereby administration to the subject suppresses GVHD, reduces the likelihood of developing GVHD, treats GVHD, or ameliorates the symptoms of GVHD in the subject.

Administration according to a method of the present invention can be systemic or local via oral or parenteral administration. For example, MEMs can be administered by intravenous injections such as drip infusions, intramuscular injections, intraperitoneal injections, intra-organ injections, or subcutaneous injections. In exemplary embodiments, administration of MEMs according to a method of the present invention occurs via intravenous injections such as drip infusions, intramuscular injections, intraperitoneal injections, intra-organ injections, or subcutaneous injections. Appropriate administration methods are selected based on a subject's age and symptoms. In exemplary embodiments, an effective dose of MEMs per administration is selected from the range of about $1\times10^6$ cells/kilogram to about $10\times10^6$ cells/kilogram of body weight of the recipient. Administration of a therapeutic agent for GVHD is once to several times a month, for example, daily, twice a week, once a week, once every two weeks, or once every four weeks. The administration schedule may be adjusted by, for example, extending the administration interval of one to three times per week to once every two weeks, once every three weeks, or once every four weeks, etc., while monitoring the subject's overall condition or symptoms associated with GVHD.

In some cases, a method of treating or preventing GVHD in a subject in need thereof comprises administering MEMs in combination with one or more active agents. Such active agents include anti-inflammatory (e.g., interleukin-2), anti-cytokine, analgesic, antipyretic, antibiotic, and antiviral agents, as well as growth factors and agonists, antagonists, and modulators of immunoregulatory agents (e.g., TNF-α, interleukin-2 (IL-2), IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Classes of pharmaceutical agents useful for treating or preventing GVHD include, without limitation, glucocorticoids (e.g., prednisone), immunosuppressants (e.g., cyclosporine, methotrexate, tacrolimus, pimecrolimus, sirolimus, mycophenolate, mofetil, visilizumab, anti-thymocyte globulin (ATG)), antineoplastics (e.g., pentostatin), and antirheumatics (e.g., hydroxychloroquine, infliximab, entanercept). Any suitable combination of such active agents is also contemplated. When administered in combination with one or more active agents, MEMs can be administered either simultaneously or sequentially with other active agents. For example, victims of acute radiation injury may simultaneously receive MEMs and one or more growth factors such as granulocyte colony stimulating factor (G-CSF), granulocyte-monocyte colony stimulating factor (GM-CSF), erythropoietin, or thrombopoietin agonists for a length of time or according to a dosage regimen sufficient to support hematopoietic recovery and to treat, alleviate, or lessen the severity of radiation-induced tissue damage.

Articles of Manufacture

In another aspect, the present invention provides articles of manufacture useful for the diagnosis, treatment, or monitoring of a radiation-induced disease or tissue damage. For example, a kit of the present invention can be used to diagnose or monitor disease progression in a subject predisposed to or suspected of developing a radiation-induced injury, or predisposed to or likely to develop GVHD. In some cases, a kit of the present invention comprises one or more vessels containing human MSC-educated macrophages and one or more reagents or other components necessary for administration of the MSC-educated macrophages to a human subject in need thereof according to a method of the invention. It may be appropriate in some cases to provide MEMs as a frozen aliquot in a pharmaceutically acceptable cryopreservant. In some cases, a kit further comprises one or more active agents including anti-inflammatory, anti-cytokine, analgesic, antipyretic, antibiotic, and antiviral agents, as well as growth factors and agonists, antagonists, and modulators of immunoregulatory agents (e.g., TNF-α, interleukin-2 (IL-2), IL-4, IL-6, IL-10, IL-12, IL-13, IL-18, IFN-α, IFN-γ, BAFF, CXCL13, IP-10, VEGF, EPO, EGF, HRG, Hepatocyte Growth Factor (HGF), Hepcidin, including antibodies reactive against any of the foregoing, and antibodies reactive against any of their receptors). Classes of pharmaceutical agents useful for treating or preventing GVHD include, without limitation, glucocorticoids (e.g., prednisone), immunosuppressants (e.g., cyclosporine, methotrexate, tacrolimus, pimecrolimus, sirolimus, mycophenolate, mofetil, visilizumab, anti-thymocyte globulin (ATG)), antineoplastics (e.g., pentostatin), and antirheumatics (e.g., hydroxychloroquine, infliximab, entanercept). Also contemplated are kits comprising suitable combinations of such active agents. Provided with such vessels are instructions for human administration and a notice in the form prescribed by a governmental agency regulating the manufacture, use, or sale of biological products, which notice reflects approval by the agency of manufacture, use, or sale for human administration.

The present invention will be more fully understood upon consideration of the following non-limiting Examples. All texts, papers, and patents disclosed herein are hereby incorporated by reference as if set forth in their entirety.

EXAMPLES

Reference is now made to the following examples, which together with the above descriptions illustrate the invention in a non-limiting fashion.

Example 1

Characterization of Macrophages and MSC-Educated Macrophages (MEMs)

To assess the in vitro phenotype of macrophages and MEMs (FIG. 1), CD14+ monocytes were isolated from peripheral blood mononuclear cells (PBMCs) from a healthy human donor. The CD14+ cells were cultured for about 7 days in a macrophage medium for differentiation into macrophages (MQs). The macrophage medium was IMDM (Iscove's Modified Dulbecco's Medium) supplemented with 10% human serum blood type AB, 1× Non-essential amino acids, 4 mM L-Glutamine, 1 mM Sodium pyruvate and 4 µg/ml recombinant human insulin. On day 5 to day 7, half of the MQs were cultured with MSCs at a 10:1 ratio for one to seven additional days, while the remaining MQs were cultured without MSCs in macrophage media for one to five days more. The resulting cells of each culture group were stained with antibodies and sorted using flow cytometry (FIG. 1A). Both MQs and MEMs were CD14+/CD90−, however MEMs had high levels of expression of CD206 and CD163.

Macrophages were assayed using flow cytometry to observe expression of CD206, CD163, CD86 and PD-L1/2 (FIG. 1B). As shown in FIG. 1B, darker and lighter histograms represents mean fluorescent intensity (MFI) in isotypes on MQs and MEMs, respectively. Dashed line and black histograms represent MFI of CD206, CD163, PD-L1 and PD-L2 in MQs and MEMs, respectively. Numbers in the plots denote the MFI value for each group with color-matched histograms. MEMs have higher CD206, CD163, PD-L1 and PD-L2 surface expression compared to MQs.

Example 2

Effects of Administering MEMs in Humanized Mouse Model of GVHD with and without Radiation An experimental mouse model for induction of xenogeneic GVHD was obtained using immunodeficient NOD/PRKDC-Scid/IL2 receptor-γ knockout (NSG) mice purchased from Jackson Lab and bred at the University of Wisconsin-Madison. On day 0, NSG mice received a dose of human peripheral blood mononuclear cells (PBMCs) intravenously (i.v.) to induce lethal xenogeneic GVHD. Some mice were randomly selected to receive 2.5 or 3 Gy irradiation (sub-lethal irradiation) on day 0 before PBMC transplant or other experiments. Some mice were randomly selected to receive irradiation after the PBMC transplant to induce inflammation (i.e., day 40). When mice developed clinical symptoms of GVHD (such as weight loss, slower activity, hunching posture, roughness of fur and skin denuding), mice were scored into four treatment groups such that each group started with the same overall GVHD clinical score (see Table 1 below). Mice were randomly selected to receive by i.v. administration PBS control (30×10⁶ in 0.2 ml i.v.), 5×10⁵ MQs, MSCs, or MEMs. Three times per week, mice in each treatment group were monitored, weighed, and scored for clinical GVHD according to the clinical scoring method set forth in Table 1. The scoring system incorporates five clinical parameters: weight loss, posture, activity, fur texture, and skin integrity (see Table 1). See, e.g., Cooke et al., *Blood* 8(8):3230-3239 (1996). As described by Cooke et al., scores of 0, 1, or 2 are assigned for each parameter, for a maximum score of 10.

TABLE 1

Assessment of Clinical GVHD in Transplanted Animals

| Criterion | Grade 0 | Grade 1 | Grade 2 |
|---|---|---|---|
| Weight loss | <10% | >10% to <25% | >25% |
| Posture | Normal | Hunching noted only at rest | Severe hunching impairs movement |
| Activity | Normal | Mild to moderately decreased | Stationary unless stimulated |
| Fur texture | Normal | Mild to moderate ruffling | Severe ruffling/poor grooming |
| Skin integrity | Normal | Scaling of paws/tail | Obvious areas of denuded skin |

For the treatment group comprising NSG mice treated with MEMs without receiving any radiation, NSG mice received an intravenous dose of human PBMCs (30×10⁶ in 0.2 ml PBS) to induce lethal xenogeneic GVHD. On day 18, when all of the mice showed clinical evidence of GVHD (based on weight loss, posture, activity, skin fur texture of the mice), mice were scored and grouped such that each of the four groups started with the same overall GVHD score. Mice received by i.v. administration: PBS; 5×10⁴ MSCs; 5×10⁴ MSCs cultured in the presence of IFNγ; or 5×10⁴ MEMs i.v. to treat GVHD. The PBS group had 5 mice/group, and each of the MSC, MSC+IFNγ, and MEM groups had 4 mice. As shown in the survival curve of FIG. 2A, administration of MEMs to NSG mice (model of xenogeneic GVHD) increased survival relative to controls (not receiving MEMs). P values for the group comparisons are provided in Table 2.

TABLE 2

P values between treatment groups.

| p values | Group comparisons |
|---|---|
| 0.024 | MEMs vs. PBS |
| 0.028 | MEMs vs. MSC |
| *0.016 | MEMs vs. MSC + IFNγ |

The experiment was repeated with larger groups of mice and with clinical GVHD scoring up to 150 days. As shown in FIG. 3 and Table 3, we observed increased survival of NSG mice treated with MSC-educated macrophages in a GVHD model without receiving any radiation relative to control mice (not receiving MEMs).

TABLE 3

Overall GVHD scores in Living Mice 147 Days Post Initial PBMC transplant.

| Group | Clinical GVHD Scores on Day 147 |
|---|---|
| PBMCs + PBS | 6 and 7 |
| PBMCs + MEMs | 1, 1, 2, 5, and 1 |

For the treatment group comprising NSG mice treated with MEMs without receiving any radiation, NSG mice received a dose of human PBMCs (30×10⁶ in 0.2 ml PBS intravenously (i.v.)) to induce lethal xenogeneic GVHD. On day 41 post PBMC transplant, the mice received 2.5 Gy total body irradiation to accelerate GVHD onset. On day 51, mice were grouped such that each group started with the same overall clinical score (5 mice in the PBS group and 6 mice in the MEM-treatment group). Mice received PBS (0.2 ml i.v.) or 5×10⁵ MEMs i.v. to treat GVHD. As shown in FIG.

2B and FIG. 4, we observed increased survival (FIG. 4A) and lower GVHD scores (FIG. 4C) in NSG mice treated with MSC-educated macrophages in a GVHD model with radiation relative to control mice (GVHD/radiation but not receiving MEMs).

Figure 9:
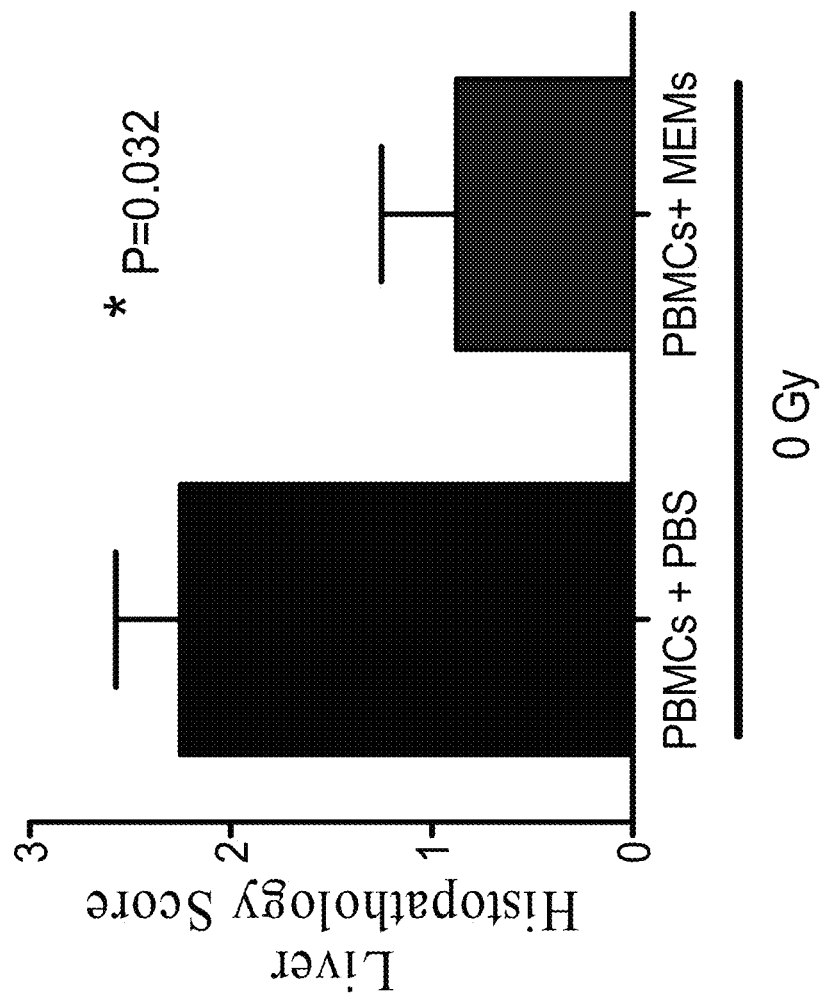
FIG. 9 presents histopathologic analysis of liver as a GVHD target organ. NSG were irradiated with a dose of 3Gy on Day+0, and injected with a lethal dose of human PBMCs ($30 \times 10^6$ in 0.2 ml PBS i.v) to induce acute xenogeneic GVHD. On Day+1 they were then treated with either a single infusion of $5 \times 10^5$ MEMs or PBS. On Day+17, livers were collected and stained by H&E for analysis by a blinded pathologist. Untreated mice (PBS) developed hepatitis consistent with T cell infiltration/injury (GVHD). MEMs showed reduced amounts of inflammation. Data analyzed by unpaired student t test.

Since the liver is a GVHD target organ, we also assayed for histopathologic liver changes. NSG were irradiated with a lethal dose of 3Gy on Day+0, and injected with a sublethal dose of human PBMCs to induce a mild acute xenogeneic GVHD. On Day+1 they were then treated with either a single infusion of $5 \times 10^5$ MEMs or PBS. On Day+17, livers were collected and stained by H&E for analysis by a blinded pathologist. As shown in FIG. 9, untreated mice (PBS) developed hepatitis consistent with T cell infiltration/injury (GVHD), but mice that received MEMs showed reduced amounts of inflammation.

Together, these data demonstrate that treatment of GVHD mice (NSG mice receiving human PBMCs) by administration of MEMs protects the mice from clinical manifestations of GVHD and increases overall survival. Also, MEM treatment is more effective for these GVHD mice (with or without radiation) than treatment with either macrophages or mesenchymal stem cells.

Example 3

Protective Effects of Administering MEMs in Mouse Model of Radiation-Induced Injury To obtain an experimental model of radiation-induced tissue damage in immunodeficient mice, CD14+ monocytes were freshly isolated from the peripheral blood of healthy human donors and cultured as above for 7 days to obtain macrophages (MQs). On day −3, MQs were maintained in a culture medium alone (undifferentiated) or grown in the presence of MSCs to generate MSC-educated-macrophages (MEMs). On day 0, NOD/PRKDC-Scid/IL2 receptor-γ knockout (NSG) mice received a lethal dose of 3 Gy total body irradiation. As shown in FIGS. 5A-D, we found that a single infusion of human MEMs on the day of the radiation insult can significantly enhance survival in an immunodeficient NSG mouse model as compared to the same number of MSCs.

We performed a separate experiment to compare no treatment and an infusion of macrophages to MEMs and MSCs. Three hours post-irradiation, the mice were divided into four groups to receive: PBS (0.2 ml i.v.), $5 \times 10^5$ MQs, $5 \times 10^5$ MSCs, or $5 \times 10^5$ MEMs i.v. The PBS group had 7 mice/group, MQ had 8 mice/group, MEM group had 10 mice/group, and MSC had 11 mice/group. The groups were assessed for evidence of protective effects against radiation-induced tissue injury. Throughout the entire experiment, mice were assessed at least 3 times per week and assigned clinical scores (see Table 1) based on activity, posture, fur texture, skin integrity, and weight loss.

Again, we found that MEMs protect mice from radiation-induced organ damage better than MSCs and led to the best overall survival. When we collected survival data up to Day 113 post irradiation, percent survival (log rank analysis up to day 113) and median survival data (median days of survival per group) were significantly increased for irradiated mice receiving MEMs relative to the other three treatment groups (FIGS. 6A-B). Similarly, weight loss and clinical scores were significantly improved for Days 20-42 (post-irradiation) for irradiated mice receiving MEMs relative to the other three treatment groups (data not shown). Based on these results, we concluded that treatment of lethally irradiated NSG mice with MEMs protects the mice from clinical manifestations of radiation-induced injury and increases overall survival. Also, MEM treatment is more effective for these irradiated mice than treatment with either macrophages or mesenchymal stem cells.

Figure 7:
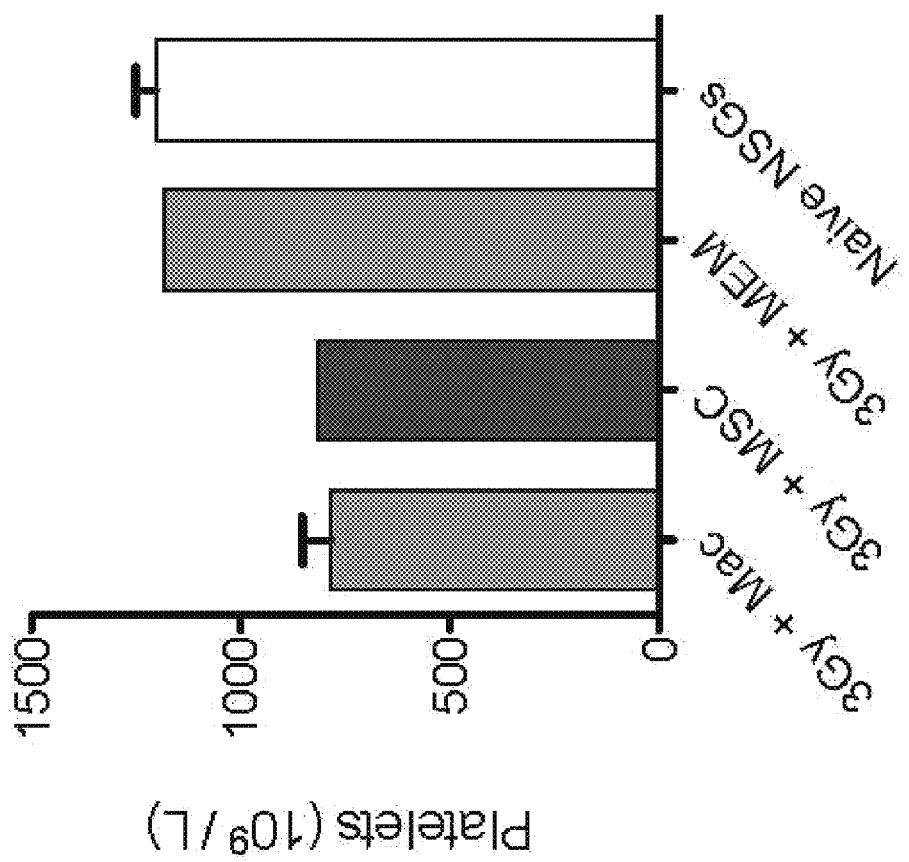
FIG. 7 presents data from treatment of lethally irradiated NSG mice with MEMs. On Day+0, NSG mice were irradiated with 3Gy total body irradiation conditioning. Then they were treated with $5 \times 10^5$ macrophages (Mac), MSCs, or MEMs. One group was left unexposed to radiation (naïve) for comparison. CBCs were collected from peripheral blood.

We also observed that MEM-treated irradiated mice exhibited comparable levels of white blood platelets to naïve, non-irradiated NSG mice (FIG. 7). For this assay, NSG mice were irradiated with 3 Gy on day 0, and then treated 3 hours post-irradiation with one of the following: $5 \times 10^5$ human MQs; $5 \times 10^5$ MSCs; or $5 \times 10^5$ MEMs. On day 44-46, peripheral blood was collected to measure the concentration of mouse complete blood counts (CBCs) and platelets.

Together, these data demonstrate that treatment of lethally irradiated NSG mice with MEMs protects host white blood cells and platelets. Also, the data suggest that MEM treatment is more effective for these irradiated mice than treatment with either macrophages or mesenchymal stem cells.

Example 4

Human MEMs as a Cell-Based Therapy for Radiation-Induced Bone Marrow Failure (BMF)

Several groups have tested the utility of mesenchymal stromal/stem cells (MSCs) as a source of hematopoietic supportive and anti-inflammatory cells to treat acute radiation syndrome (1-5). While MSCs do have reparative properties that are needed after radiation injury (6) and have shown efficacy in preclinical models, MSCs have not consistently improved BMF and are not yet approved for clinical use for radiation-induced BMF. Aside from MSCs, infusions of myeloid progenitor cells have been found in mouse models to prolong survival after acute radiation syndrome (7), but again the specific impact on the hematopoietic niche and BMF is unknown.

Figure 10:
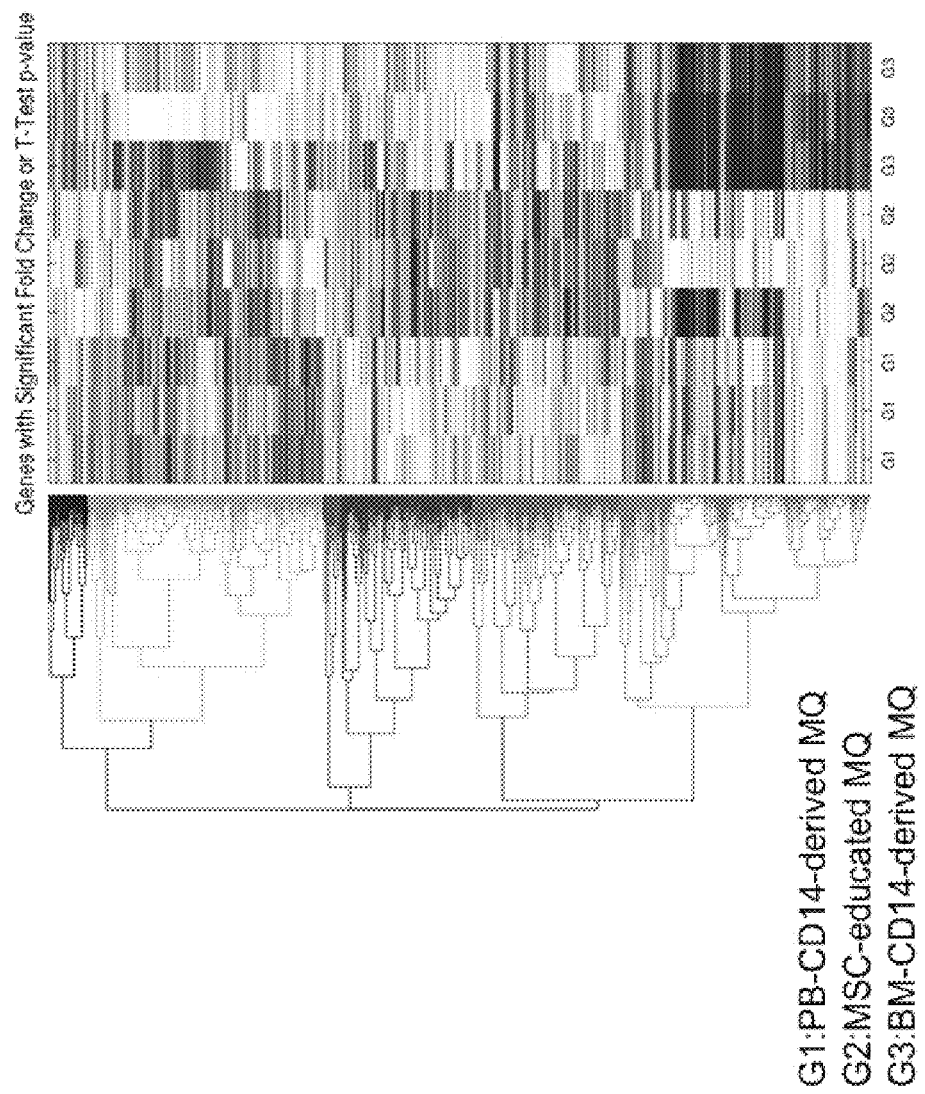
FIG. 10 is a RNA-seq heat-map demonstrating that MEMs express a unique gene expression profile that distinguishes them from macrophages cultured from peripheral blood (PB) or bone marrow (BM). CD14$^+$ monocytes were cultured from PBMCs and BM cells without cytokines for 1 week, causing monocytes to adhere to flasks, forming macrophages (MQ). MSC-educated MQ (MEMs) were cultured by incubating PB-derived MQ with MSCs at a 10:1 ratio for 3 days. CD14$^+$ sorted macrophages were obtained from PB, MEM and BM cultures and RNA was isolated for RNA-SEQ. Hierarchal clustering analysis demonstrates genes that show a significantly higher (red) or lower (blue) expression. The 3 sources of macrophages show six gene clusters (color coded on the left) are identified based on the gene expression pattern, demonstrating that MEMs are a distinct subset of MQ. Red depicts genes that are upregulated and blue depicts genes that are donwregulated. Groups were compared using a standard t test, and a p<0.05 was considered significant.

Because other models suggested murine or human MSCs could polarize macrophages into a M2 phenotype (8-11), we wanted to determine whether MEMs were M2 macrophages or a distinct subset. Again, because M2 macrophages produce low levels of IL-6 and MEMs produce high levels of IL-6, we believe MEMs are a separate cell subset different that previously described M2 macrophages but we have also searched for other potential markers to distinguish these cells. Using RNA-Seq analysis of 3 cell subsets: peripheral blood-derived macrophages, MEMs, and bone marrow derived macrophages, we determined that MEMs had a gene expression signature distinct from macrophages (FIG. 10).

Figure 8:
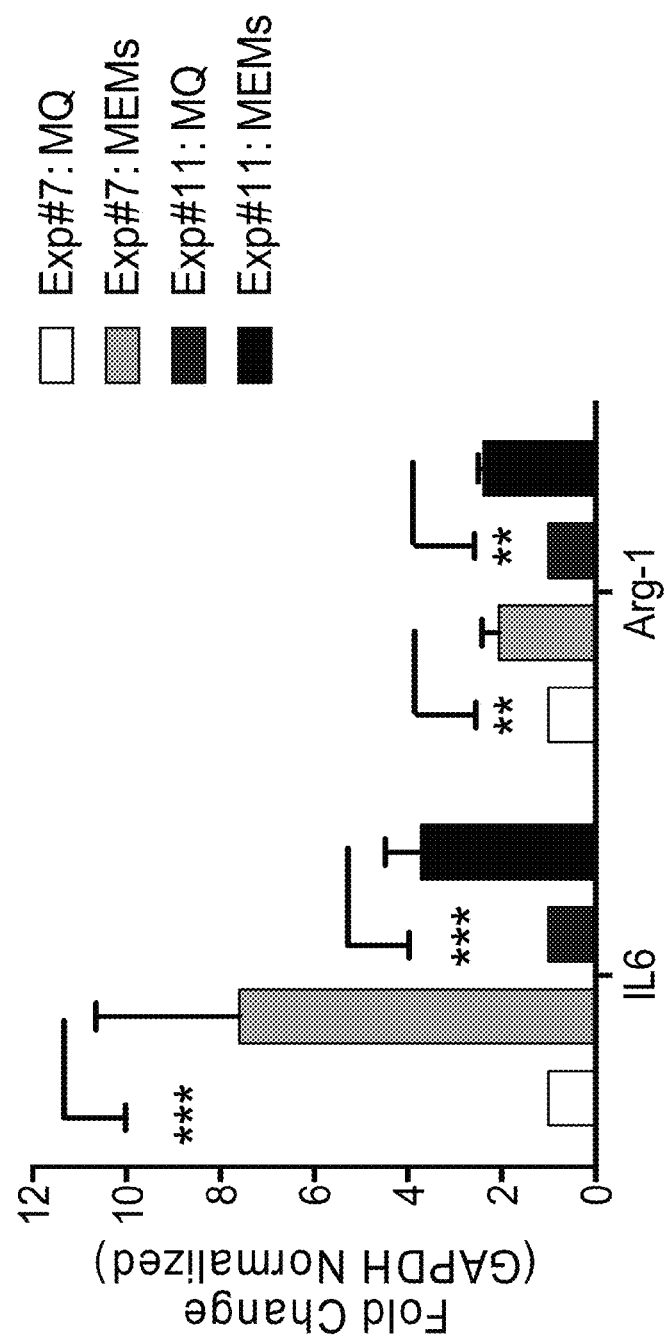
FIG. 8 demonstrates increased gene expression of IL-6 and arginase-1 in MEMs. Human PBMCs were collected from a healthy donor, monocytes were isolated and grown in media without cytokines for 1 week. Then either media or MSCs were added for 3 days, converting the monocytes to macrophages (MQ) or MEMs respectively. The CD14$^+$ cells were sorted from the MEM group to eliminate contaminating MSCs, then RNA was isolated from each group. RT-PCR for IL-6 and Arginase-1 expression was performed and depicting the fold change expression after normalization to the GAPDH housekeeping gene. Data illustrated from two separate experiments from 2 separate healthy donors. =p<0.01, *=p<0.001 (Mean±SEM by two way ANOVA of analysis with Dunnett's multiple comparison post test).

We next chose select genes that showed significantly increased gene expression and verified their expression by RT-PCR. As shown in FIG. 8, human MEMs exhibit increased gene expression of IL-6 and arginase-1, which is a molecule overexpressed by alternatively activated, immunosuppressive M2 macrophages.

REFERENCES

1. Eaton and Varney, Mesenchymal stem cell therapy for acute radiation syndrome: innovative medical approaches in military medicine. *Military Medical Res.* 2015; 2:2.
2. Hu et al., The radiation protection and therapy effects of mesenchymal stem cells in mice with acute radiation injury. *The British J. Radiology* 2010; 83(985): 52-58.

3. Lange et al., *PloS one* 2011; 6(1):e14486.
4. Shim et al., Mitigating effects of hUCB-MSCs on the hematopoietic syndrome resulting from total body irradiation. *Experimental Hematology* 2013; 41(4):346-353 e342.
5. Hu et al., *PLoS One* 2013; 8(11):e78227.
6. Le Blanc and Mougiakakos, Multipotent mesenchymal stromal cells and the innate immune system. *Nat Rev Immunol* 2012; 12(5):383-396.
7. Singh et al., Myeloid progenitors: a radiation countermeasure that is effective when initiated days after irradiation. *Radiat Res* 2012; 177(6):781-791.
8. Nemeth et al., *Nat Med* 2009; 15(1):42-49.
9. Maggini et al., Mouse bone marrow derived mesenchymal stromal cells turn activated macrophages into a regulatory-like profile. *PLoS One* 2010; 5(2):e9252.
10. Zhang et al., Human gingiva-derived mesenchymal stem cells elicit polarization of m2 macrophages and enhance cutaneous wound healing. *Stem Cells* 2010; 28(10): 1856-1868.
11. Francois et al., Human MSC suppression correlates with cytokine induction of indoleamine 2,3-dioxygenase and bystander M2 macrophage differentiation. *Mol Ther* 2012; 20(1):187-195.

We claim:

1. A method for treating bone marrow failure in a subject exposed to ionizing radiation, the method comprising administering to the subject a therapeutically effective amount of human IL-6 high, IL-10 high, IL-12 low, and TNF-α low mesenchymal stem cell-educated macrophages (MEMs), whereby the MEM-administered subject maintains production of white blood cells and platelets after exposure to ionizing radiation.

2. The method of claim 1, wherein the ionizing radiation exposure is a consequence of radiation therapy or accidental radiation exposure.

3. The method of claim 1, wherein the subject is exposed to ionizing radiation prior to administering MEMs.

4. The method of claim 1, wherein the MEMs are administered in a pharmaceutical composition comprising MEMs and a pharmaceutically acceptable carrier.

5. The method of claim 1, wherein the MEMs are administered by intravenous injection or by injection directly to a site of radiation exposure.

6. The method of claim 1, wherein the therapeutically effective amount of MEMs is between about $1 \times 10^6$ cells/kilogram to about $10 \times 10^6$ cells/kilogram of body weight of the subject.

7. The method of claim 1, wherein the MEMs are PD-L1 high and PD-L2 high.

8. The method of claim 1, wherein the subject is exposed to a myeloablative dose of ionizing radiation.

* * * * *